(12) United States Patent
Egesborg et al.

(10) Patent No.: US 11,684,724 B2
(45) Date of Patent: Jun. 27, 2023

(54) AUTO INJECTOR WITH VARIABLE PLUNGER FORCE

(71) Applicant: Ascendis Pharma A/S, Hellerup (DK)

(72) Inventors: Henrik Egesborg, Hellerup (DK); Steen Jensen, Dragør (DK); Martin Nørgaard Larsen, Viborg (DK); Johnny Elkjær, Struer (DK); Bjørn Knud Andersen, Struer (DK)

(73) Assignee: Ascendis Pharma A/S, Hellerup (DK)

( * ) Notice: Subject to any disclaimer, the term of this patent is extended or adjusted under 35 U.S.C. 154(b) by 139 days.

(21) Appl. No.: 16/607,342

(22) PCT Filed: May 23, 2018

(86) PCT No.: PCT/EP2018/063460
§ 371 (c)(1),
(2) Date: Oct. 22, 2019

(87) PCT Pub. No.: WO2018/215516
PCT Pub. Date: Nov. 29, 2018

(65) Prior Publication Data
US 2020/0384207 A1 Dec. 10, 2020

(30) Foreign Application Priority Data
May 23, 2017 (EP) .................. 17172456

(51) Int. Cl.
*A61M 5/315* (2006.01)
*A61M 5/19* (2006.01)
*A61M 5/20* (2006.01)

(52) U.S. Cl.
CPC .......... *A61M 5/31576* (2013.01); *A61M 5/19* (2013.01); *A61M 5/20* (2013.01);
(Continued)

(58) Field of Classification Search
CPC .... A61M 5/31576; A61M 2005/31588; A61M 2205/332; A61M 5/19; A61M 5/20
See application file for complete search history.

(56) References Cited

U.S. PATENT DOCUMENTS

| 4,024,864 A | 5/1977 | Davies |
| 4,677,980 A | 7/1987 | Reilly et al. |

(Continued)

FOREIGN PATENT DOCUMENTS

| CN | 101905048 | 12/2010 |
| CN | 102413855 | 4/2012 |

(Continued)

OTHER PUBLICATIONS

English translation of Office Action issued in Japanese Application No. 2019-570894, dated Jan. 13, 2022.
(Continued)

*Primary Examiner* — Theodore J Stigell
(74) *Attorney, Agent, or Firm* — Knobbe, Martens, Olson & Bear, LLP

(57) ABSTRACT

Disclosed is a method and an auto-injector for administering a medicament. The auto injector comprising: a housing; a cartridge receiver configured to receive a cartridge comprising a first stopper; a drive module coupled to move a plunger rod between a retracted plunger rod position and an extended plunger rod position, the plunger rod being configured to move the first stopper; a resistance sensor configured to provide a resistance signal indicative of resistance against movement of the plunger rod; and a processing unit coupled to the drive module and to the resistance sensor. The processing unit being configured to: control the drive module to move the plunger rod towards the extended plunger rod position with a plunger rod speed; determine plunger rod position; receive the resistance signal; and control the drive module to adjust movement of the plunger rod if the (Continued)

resistance signal is indicative of resistance against movement of the plunger rod above a high resistance threshold, wherein the high resistance threshold is based on the plunger rod position.

25 Claims, 13 Drawing Sheets

(52) U.S. Cl.
CPC ............ *A61M 2005/31588* (2013.01); *A61M 2205/332* (2013.01); *A61M 2205/3331* (2013.01); *A61M 2205/3365* (2013.01); *A61M 2205/50* (2013.01); *A61M 2205/6072* (2013.01); *A61M 2205/6081* (2013.01); *A61M 2205/8206* (2013.01)

(56) References Cited

U.S. PATENT DOCUMENTS

| | | | |
|---|---|---|---|
| 5,739,508 | A | 4/1998 | Uber, III |
| 5,808,203 | A | 9/1998 | Nolan, Jr. et al. |
| 6,368,314 | B1* | 4/2002 | Kipfer ............... A61M 5/14546 604/67 |
| 9,173,995 | B1 | 11/2015 | Tucker |
| 10,384,031 | B1 | 8/2019 | Acker et al. |
| 10,835,677 | B2 | 11/2020 | Fabricius et al. |
| 11,179,524 | B2 | 11/2021 | Pedersen et al. |
| 11,351,305 | B2 | 6/2022 | Pedersen et al. |
| 11,406,760 | B2 | 8/2022 | Olesen et al. |
| 11,517,673 | B2 | 12/2022 | Pedersen et al. |
| 11,524,115 | B2 | 12/2022 | Jacobsen et al. |
| 2002/0016573 | A1 | 2/2002 | Munk |
| 2002/0107477 | A1 | 8/2002 | Kipfer |
| 2003/0083626 | A1 | 5/2003 | Munk et al. |
| 2003/0205587 | A1 | 11/2003 | Tribe |
| 2005/0261634 | A1 | 11/2005 | Karlsson |
| 2006/0178630 | A1 | 8/2006 | Bostrom et al. |
| 2009/0036846 | A1 | 2/2009 | Dacquay et al. |
| 2009/0209883 | A1 | 8/2009 | Higgins et al. |
| 2009/0299328 | A1 | 12/2009 | Mudd et al. |
| 2010/0069842 | A1 | 3/2010 | Dos Santos et al. |
| 2010/0094309 | A1* | 4/2010 | Boukhny ................ A61F 2/167 606/107 |
| 2010/0211005 | A1 | 8/2010 | Edwards et al. |
| 2011/0313395 | A1 | 12/2011 | Krulevitch et al. |
| 2012/0078185 | A1 | 3/2012 | Smith et al. |
| 2012/0283655 | A1 | 11/2012 | Plumptre et al. |
| 2013/0079708 | A1 | 3/2013 | Wiimpenny et al. |
| 2013/0193073 | A1 | 8/2013 | Hogard et al. |
| 2013/0211326 | A1 | 8/2013 | Dasbach et al. |
| 2013/0211327 | A1 | 8/2013 | Osman et al. |
| 2013/0226134 | A1 | 8/2013 | Schabbach et al. |
| 2013/0245545 | A1 | 9/2013 | Arnold et al. |
| 2013/0281965 | A1 | 10/2013 | Kamen et al. |
| 2013/0296807 | A1 | 11/2013 | Lintern et al. |
| 2014/0012229 | A1 | 1/2014 | Bokelman et al. |
| 2014/0114277 | A1 | 4/2014 | Eggert et al. |
| 2014/0142514 | A1 | 5/2014 | Elahi et al. |
| 2014/0166915 | A1 | 6/2014 | Ishibashi et al. |
| 2014/0188076 | A1 | 7/2014 | Kamen et al. |
| 2014/0193788 | A1 | 7/2014 | Groves et al. |
| 2014/0207106 | A1 | 7/2014 | Bechmann et al. |
| 2014/0221925 | A1 | 8/2014 | Kondoh et al. |
| 2014/0358093 | A1 | 12/2014 | Soerensen et al. |
| 2015/0045729 | A1 | 2/2015 | Denzer et al. |
| 2015/0051538 | A1* | 2/2015 | Hata ................... A61M 5/1452 604/154 |
| 2015/0088089 | A1 | 3/2015 | Bartlett, II et al. |
| 2015/0231334 | A1 | 8/2015 | Buchine et al. |
| 2015/0306316 | A1* | 10/2015 | Bruggemann .......... A61M 5/20 604/67 |
| 2015/0320932 | A1 | 11/2015 | Draper et al. |
| 2015/0359967 | A1 | 12/2015 | Steel et al. |
| 2015/0367074 | A1 | 12/2015 | Draper et al. |
| 2015/0367075 | A1 | 12/2015 | Cave |
| 2017/0196702 | A1 | 7/2017 | Agarwal |
| 2018/0094309 | A1 | 4/2018 | Boukhany |
| 2018/0369481 | A1 | 12/2018 | Pedersen et al. |
| 2018/0369482 | A1 | 12/2018 | Pedersen et al. |
| 2018/0369483 | A1 | 12/2018 | Olesen et al. |
| 2019/0009028 | A1 | 1/2019 | Jacobsen et al. |
| 2019/0009029 | A1 | 1/2019 | Fabricius et al. |
| 2019/0224419 | A1 | 7/2019 | Pedersen et al. |
| 2022/0152310 | A1 | 5/2022 | Pedersen et al. |
| 2022/0288316 | A1 | 9/2022 | Olesen et al. |

FOREIGN PATENT DOCUMENTS

| | | |
|---|---|---|
| CN | 103813820 | 5/2014 |
| CN | 105492047 | 4/2016 |
| EP | 2656865 | 10/2013 |
| EP | 2777731 | 9/2014 |
| EP | 2923715 | 9/2015 |
| GB | 2356349 | 5/2001 |
| GB | 2506918 | 4/2014 |
| JP | H11513586 | 11/1999 |
| JP | 2000-513973 | 10/2000 |
| JP | 2005-080832 | 3/2005 |
| JP | 2008-531235 | 8/2008 |
| JP | 2009-279438 | 12/2009 |
| JP | 2010-506681 | 3/2010 |
| JP | 2010-510011 | 4/2010 |
| JP | 2010-523181 | 7/2010 |
| JP | 2011-507668 | 3/2011 |
| JP | 2011-521744 | 7/2011 |
| JP | 2011-240159 | 12/2011 |
| JP | 2012-505066 A | 3/2012 |
| JP | 2012-066767 | 4/2012 |
| JP | 2012-516737 | 7/2012 |
| JP | 2012-519028 A | 8/2012 |
| JP | 2013-506444 | 2/2013 |
| JP | 2013-069305 | 4/2013 |
| JP | 2013-075154 A | 4/2013 |
| JP | 2013-537844 | 10/2013 |
| JP | 2014-500746 | 1/2014 |
| JP | 2014-502890 | 2/2014 |
| JP | 2014-506159 | 3/2014 |
| JP | 2014-507223 | 3/2014 |
| JP | 2014-515941 | 7/2014 |
| JP | 2014-516700 | 7/2014 |
| JP | 2014-516702 | 7/2014 |
| JP | 2014-521113 | 8/2014 |
| JP | 2014-4528787 | 10/2014 |
| JP | 2015-521920 | 8/2015 |
| JP | 2015-163208 | 9/2015 |
| JP | 2016-208611 | 12/2016 |
| KR | 10-2015-0125701 | 11/2015 |
| KR | B-10-1666755 | 10/2016 |
| RU | 2014-120469 | 11/2015 |
| WO | WO 02/051471 | 7/2002 |
| WO | WO 2005/102416 | 11/2005 |
| WO | WO 2006/116997 | 11/2006 |
| WO | WO 2008/062025 | 5/2008 |
| WO | WO 2006/059597 | 6/2008 |
| WO | WO 2010/098927 | 9/2010 |
| WO | WO-2010/098931 * | 9/2010 |
| WO | WO 2010/098931 A1 | 9/2010 |
| WO | WO 2012/112347 | 8/2012 |
| WO | WO 2010/100883 | 9/2012 |
| WO | WO 2012/160157 | 11/2012 |
| WO | WO 2013/065055 | 5/2013 |
| WO | WO 2013/138830 | 9/2013 |
| WO | WO 2012/066767 | 5/2014 |
| WO | WO 2014/144096 | 9/2014 |
| WO | WO 2014/166915 | 10/2014 |
| WO | WO 2014/168205 | 10/2014 |
| WO | WO 2014/187812 | 11/2014 |
| WO | WO 2014/187813 | 11/2014 |
| WO | WO 2015/006430 A1 | 1/2015 |
| WO | WO 2013/069305 | 4/2015 |
| WO | WO 2015/055640 | 4/2015 |
| WO | WO 2015/055642 | 4/2015 |

(56) References Cited

FOREIGN PATENT DOCUMENTS

| WO | WO 2015/115326 | 8/2015 |
|---|---|---|
| WO | WO 2015/187797 | 12/2015 |
| WO | WO 2016/005421 | 1/2016 |
| WO | WO 2016/033507 | 3/2016 |
| WO | WO 2016/098060 | 6/2016 |
| WO | WO 2014/091765 | 1/2017 |
| WO | WO 2017/114906 | 7/2017 |
| WO | WO 2017/114907 | 7/2017 |
| WO | WO 2017/114908 | 7/2017 |
| WO | WO 2017/114909 | 7/2017 |
| WO | WO 2017/114910 | 7/2017 |
| WO | WO 2017/114911 | 7/2017 |
| WO | WO 2017/114912 | 7/2017 |
| WO | WO 2018/215516 | 11/2018 |
| WO | WO 2019/002534 | 1/2019 |

OTHER PUBLICATIONS

International Search Report for PCT/EP2018/063460 dated Jul. 3, 2018.
English Translation of Office Action dated Jun. 3, 2021, in Corresponding Chinese Application No. 201880043795.0.
English Translation of Office Action dated Jul. 9, 2021, in corresponding Russian Application No. 2019140269.
English Translation of Office Action dated Jul. 30, 2021, in corresponding Russian Application No. 2020103216.
English Translation of Office Action dated Jun. 10, 2021, in corresponding Chinese Application No. 201880033657.4.
Office Action issued in Japanese Application No. 2019-565323, dated Jan. 5, 2022.
European Search Report for EP 15203132.4, dated Jun. 29, 2016.
European Search Report for EP 15203137.3, dated Jul. 1, 2016.
Partial European Search Report for EP15203168.8, dated Sep. 16, 2016.
International Search Report for PCT/EP2016/082861, dated Mar. 22, 2017.
International Preliminary Report on Patentability for PCT/EP2016/082861, dated Jul. 12, 2018.
International Search Report for PCT/EP2016/082856, dated Mar. 28, 2017.
International Preliminary Report on Patentability for PCT/EP2016/082856, dated Jul. 12, 2018.
International Search Report for PCT/EP2016/082860, dated May 3, 2017.
International Preliminary Report on Patentability for PCT/EP2016/082860, dated Jul. 12, 2018.
International Search Report for PCT/EP2016/082858, dated Mar. 24, 2017.
International Preliminary Report on Patentability for PCT/EP2016/082858, dated Jul. 12, 2018.
International Search Report for PCT/EP2016/082855, dated Mar. 24, 2017.
International Preliminary Report on Patentability for PCT/EP2016/082855, dated Jul. 12, 2018.
International Search Report for PCT/EP2016/082857, dated May 12, 2017.
International Preliminary Report on Patentability for PCT/EP2016/082857, dated Jul. 12, 2018.
International Search Report for PCT/EP2016/082859, dated Apr. 10, 2017.
International Preliminary Report on Patentability for PCT/EP2016/082859, dated Jul. 12, 2018.
International Preliminary Report on Patentability for PCT/EP2018/063460, dated Dec. 5, 2019.
International Search Report for PCT/EP2018/067532, dated Sep. 25, 2018.
International Preliminary Report on Patentability for PCT/EP2018/067532, dated Jan. 9, 2020.
English translation of Office Action issued in Chinese Application No. 201880033657, dated Feb. 23, 2022.
English translation of Office Action issued in Japanese Application No. 2021-116315, dated Sep. 2, 2022.
English translation of Office Action issued in Korean Application No. 10-2020-7000564, dated Oct. 17, 2022.

\* cited by examiner

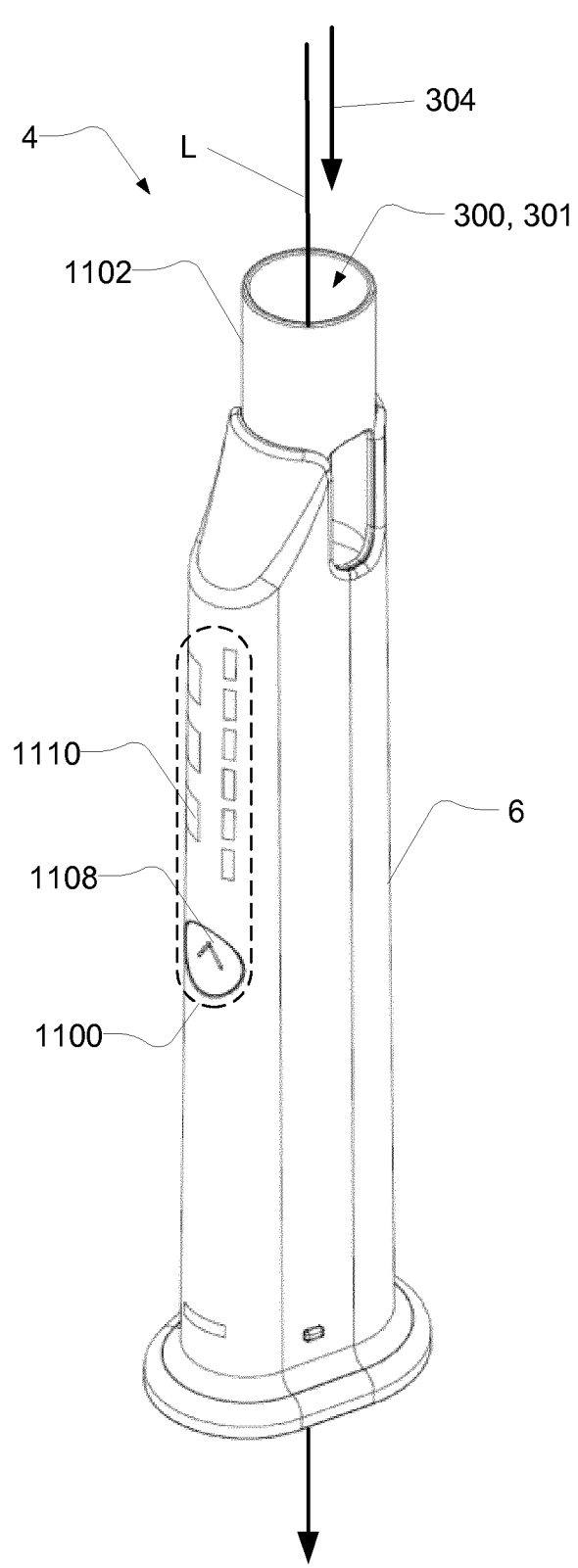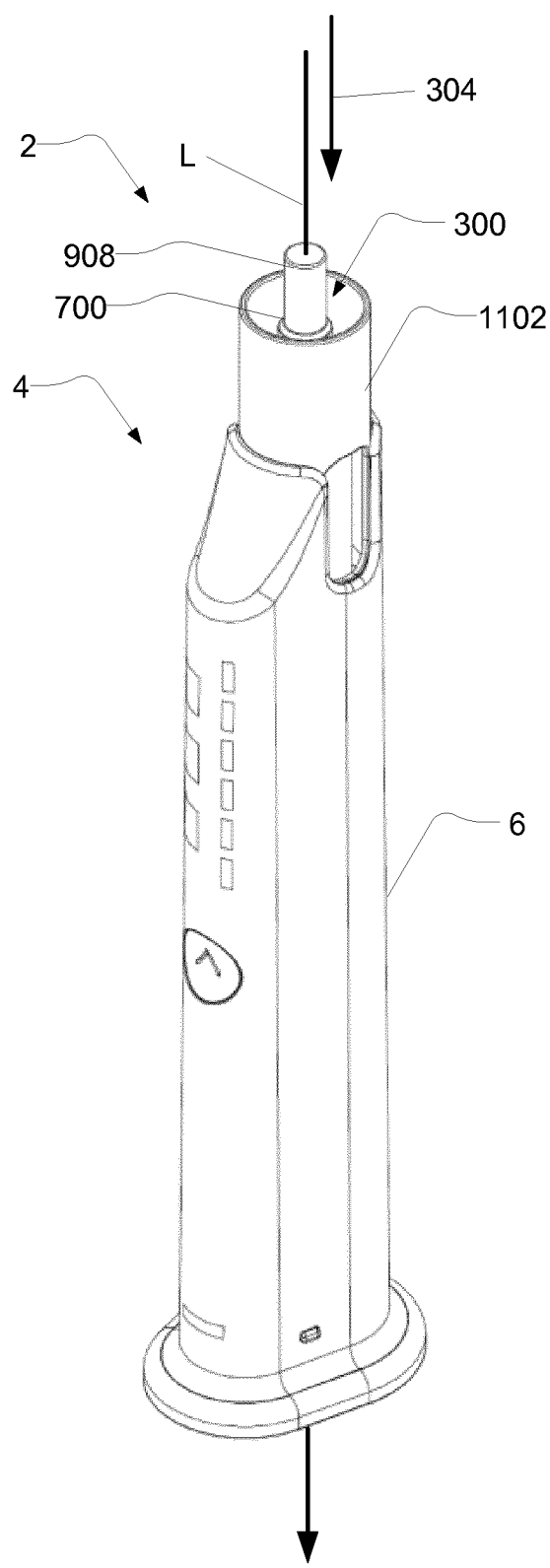

AUTO INJECTOR WITH VARIABLE PLUNGER FORCE

CROSS REFERENCE TO RELATED APPLICATIONS

This application is a U.S. National Phase Application of PCT International Application Number PCT/EP2018/063460, filed on May 23, 2018, designating the United States of America and published in the English language, which is an International Application of and claims the benefit of priority to European Patent Application No. 17172456.0, filed on May 23, 2017. The disclosures of the above-referenced applications are hereby expressly incorporated by reference in their entireties.

The present disclosure relates to an auto injector, such as an electronic auto injector, a system comprising an auto injector and a cartridge, and a method for operating an auto injector.

BACKGROUND

Hypodermic syringes are widely used to deliver fluids to the body. It is known to have hypodermic syringes applicable for manual operation. However, auto injectors, such as electronic auto injectors, have been developed and are widely used to aid the administering of fluid or medicaments to the body.

To avoid relying on users correctly performing certain tasks, it is of increasing interest that the auto injector automatically carries out as much as possible of the injection process.

However, for safety of the user, it is of continuous desire that such auto injector prevents adverse use, securing or facilitating that the medicament is given appropriately, and that erroneous usage, or results of erroneous usage, e.g. incorrect dosage or transmission of infections, is prevented or reduced.

It is of further importance to enable precise control of the amount of medicament being injected and/or absorbed by the tissue. Thus, it is of increasing interest to decrease the risk of medicament leaking or being spilled, and furthermore also to decrease the amount of residual medicament in the cartridge following end of injection.

The plunger force may often be limited in order to avoid back-flush of medicament during injection, i.e. that medicament flows backwards around the stopper as oppose to being expelled through the needle. Other objectives might also motivate for plunger force limitation, e.g. for preventing medicament leakage or even to prevent breakage of a cartridge structure.

SUMMARY

Despite the known solutions there is a need for an auto injector and associated method for optimizing dosing accuracy, such as by decreasing residual medicament following injection, and preventing medicament leakage, such as through or around an end stopper of the cartridge.

Accordingly, an auto injector for administering a medicament is disclosed. The auto injector comprising: a housing, a cartridge receiver, a drive module, a resistance sensor, and a processing unit.

The cartridge receiver is configured to receive a cartridge comprising a first stopper. The drive module is coupled to move, such as advance, a plunger rod between a retracted plunger rod position and an extended plunger rod position. The plunger rod is configured to move, such as advance, the first stopper.

The resistance sensor is configured to provide a resistance signal indicative of resistance against movement of the plunger rod.

The processing unit is coupled to the drive module. The processing unit is coupled to the resistance sensor.

The processing unit is configured to: control the drive module to move, such as advance, the plunger rod towards the extended plunger rod position with a plunger rod speed; determine plunger rod position; receive the resistance signal; and control the drive module to adjust movement of the plunger rod if the resistance signal is indicative of resistance against movement of the plunger rod above a high resistance threshold. The high resistance threshold is based on the plunger rod position.

The housing may accommodate one or more of the cartridge receiver, the drive module, the resistance sensor and the processing unit.

Also disclosed is a system. The system comprises the auto injector and the cartridge comprising the first stopper, wherein the cartridge is configured to be received in the cartridge receiver.

Also disclosed is a method for controlling an auto injector. The method comprises: receiving a cartridge comprising a first stopper; moving a plunger rod towards an extended plunger rod position with a plunger rod speed; determining plunger rod position; receiving a resistance signal indicative of resistance against movement of the plunger rod; and adjusting movement of the plunger rod if the resistance signal is indicative of resistance against movement of the plunger rod above a high resistance threshold, wherein the high resistance threshold is based on the plunger rod position.

It is an advantage of the present disclosure that it provides a way of optimizing dosing accuracy through more fully emptying a drug cartridge during injection by applying more force to the stopper(s)—and maintain such elevated force over a period of time—thereby forcing deformation/compression of the stopper to better contact with (fill out) the interior cartridge shoulder area and thereby press out residual drug sitting here. Additionally, the disclosed approach also provides an improved medicament utilization as less medicament may be wasted from each cartridge.

Plunger rod speed may further be optimized, e.g. leading to an optimization of the time of the injection procedure, e.g. time needed to inject the medicament and/or in preparing for injection.

It is a further advantage of the present disclosure, that patient safety is increased, e.g. by decreasing the risk of incorrect dosage of medicament.

Furthermore, the present disclosure provides the advantage of allowing for improved precision of medicament usage, and allowing for reducing the amount of medicament not being used. Thus, a further advantage of the present disclosure is that cost of not used medicament may be reduced.

The high resistance threshold may be based on the plunger rod position. The high resistance threshold may be a first high resistance threshold and/or a second high resistance threshold and/or third high resistance threshold.

The processing unit may be configured to determine the high resistance threshold, e.g. based on the plunger rod position.

The high resistance threshold may be a first high resistance threshold when the plunger rod position is between the retracted plunger rod position and a first plunger rod position. Alternatively or additionally, the high resistance threshold may be a second high resistance threshold when the plunger rod position is between a second plunger rod position and the extended plunger rod position.

The second high resistance threshold may be higher than the first high resistance threshold. When the second high resistance threshold corresponds to an extended plunger rod position at the end of the injection of the medicament, the high resistance threshold may be higher in order to ensure effective emptying of the cartridge without the risk of leakage at the stoppers or the septum at the end of injection because of the lower needle flow resistance contribution to the pressure in the cartridge.

The first high resistance threshold may be between 50-80 N, such as 50 N, 55 N, 60 N, 65 N, 70 N, 75 N, or 80 N. In an example, the first high resistance threshold is 55 N.

The second high resistance threshold may be between 70-100 N, such as between 75-85 N, or such as between 80-90 N, or such as 70 N, 75 N, 80 N, 85 N, or 90 N. In an example, the second high resistance threshold is 80 N.

The high resistance threshold may be a third high resistance threshold when the plunger rod position is between the first plunger rod position and the second plunger rod position. The high resistance threshold may be the third high resistance threshold when the plunger rod position is at a third plunger rod position. The third plunger rod position may be between the first plunger rod position and the second plunger rod position.

The third high resistance threshold may be higher than the first high resistance threshold. The third high resistance threshold may be lower than the second high resistance threshold. The third high resistance threshold may be between the first high resistance threshold and the second high resistance threshold.

The high resistance threshold, e.g. the third high resistance threshold, may be increasing as the plunger rod position is moved from the first plunger rod position to the second plunger rod position.

The distance between the extended plunger rod position and the first plunger rod position may be between 1-3 mm, such as 2 mm.

The distance between the retracted plunger rod position and the first plunger rod position may be between 0-60 mm.

The distance between the retracted plunger rod position and the first plunger rod position may be between 50-60 mm, such as 55 mm, 56 mm, or 57 mm.

The auto injector may comprise a code sensor. The code sensor may be configured to read a cartridge code feature, such as a cartridge code feature of the cartridge and/or attached to the cartridge. The code sensor may be configured to transmit a code signal indicative of the cartridge code feature. The code sensor may be configured to read the cartridge code feature in a plurality of positions. The cartridge code sensor may be movable. The cartridge code sensor may comprise a plurality of sensors, such as a plurality of transmitters and/or receivers.

The code sensor may comprise an optical sensor. The code sensor may comprise an optical sensor comprising a transmitter and a receiver, such as a light transmitter and a light receiver. The code sensor may be configured to read the cartridge code feature. The code sensor may be configured to read QR codes, bar codes, colour codes, and/or any combination hereof.

The processing unit may be coupled to the code sensor. The processing unit may be configured to receive from the code sensor a code signal indicative of the cartridge code feature. The processing unit may be configured to determine a plunger rod position, such as the first plunger rod position and/or the second plunger rod position, based on the code signal.

The resistance sensor may be configured to measure pressure and/or force applied to a plunger rod front end of the plunger rod. The plunger rod front end may be configured to engage with the first stopper of the cartridge. The resistance sensor may be configured to measure pressure and/or force between the plunger rod and the stopper. For example, the resistance sensor may comprise a pressure transducer and/or a force transducer on the plunger rod front end. The plunger rod may comprise the resistance sensor.

Alternatively or additionally, The resistance sensor may be configured to determine electrical current through the drive module, and/or configured to determine electrical power consumed by the drive module. For example, the resistance sensor may be configured to measure electrical resistance, electrical current, and/or electrical voltage of the drive module. The resistance sensor may comprise an electrical resistance sensor, an electrical current sensor, and/or an electrical voltage sensor. The resistance signal may be based on electrical power consumed by the drive module, such as on the determined electrical power consumed by the drive module. The resistance signal may be based on electrical current through the drive module, such as on the measured electrical current through the drive module. The drive module may comprise the resistance sensor.

Instead of applying a dedicated force sensor, e.g. due to cost and architectural complexity of applying such a force sensor between a plunger and a cartridge stopper, a practical way to monitor equivalent plunger force and/or resistance may be through monitoring the current through the drive module, such as through the motor of the drive module. For electromechanical systems, this will correlate well to output force. The force acting upon an inductor inside a magnetic field can be expressed as $F=B*l*I$, where B is the magnetic field strength, I is the inductor current and l is the length of the inductor in the magnetic field.

The auto injector may be an electronic auto injector. The auto injector may comprise a battery. The housing may accommodate the battery. The battery may be a rechargeable battery. For example, the battery may be a Li-ion battery or a NiCd battery or a NiMH battery. The battery may be configured to be charged by connection of a charger.

The drive module may comprise one or more electrical elements. The drive module may be configured to receive electrical power from the battery. The drive module may be electrically connected to the battery for receiving electrical power. The drive module may comprise a motor, such as an electro-mechanical motor, such as a DC motor, e.g. a DC motor with or without brushes. The drive module may comprise a solenoid motor. The drive module may comprise a shape memory metal engine. The drive module may comprise an arrangement of springs configured to actuate the plunger rod. The drive module may comprise a pressurized gas configured to actuate the plunger rod.

The cartridge, e.g. a cartridge compartment of the cartridge, may comprise medicament. The movement of the first stopper may be to expel medicament from the cartridge, such as from the cartridge compartment, through a cartridge outlet and/or to expel air from the cartridge, such as from the cartridge compartment, through the cartridge outlet.

The plunger rod position, such as a present plunger rod position, such as the plunger rod position at a specific moment in time, may be determined, e.g. by the processing unit. The plunger rod position may be determined based on detection from a sensor, such as a plunger rod position sensor.

The auto injector may comprise the plunger rod position sensor. The plunger rod position sensor may be configured to detect the position of the plunger rod and/or the position of the first stopper. The drive module may comprise the plunger rod position sensor.

The Auto Injector may comprise a tachometer. The plunger rod position sensor may comprise the tachometer. The plunger rod position sensor may be a tachometer. The tachometer may be configured to count the revolutions of the drive module, such as a motor of the drive module, such as the revolutions of the drive module from a set point, such as a point wherein the position of the plunger rod is known, such as the retracted plunger rod position, such as a fully retracted position of the plunger rod. The count of revolutions of the drive module may be used to determine the plunger rod position, i.e. the position of the plunger rod at a specific moment in time.

The tachometer may be configured to provide a tachometer signal indicative of a count of revolutions of the drive module. The processing unit may be coupled to the tachometer. The processing unit may be configured to receive the tachometer signal. The processing unit may be configured to determine the present plunger rod position based on the tachometer signal.

The processing unit may be coupled to the plunger rod position sensor. The processing unit may receive from the plunger rod position sensor a first plunger rod position sensor signal, such as the tachometer signal, indicative of the count of revolutions of the drive module. The processing unit may determine the position of the plunger rod based on the first plunger rod position sensor signal, e.g. the tachometer signal. The processing unit may receive a second plunger rod position sensor signal, e.g. from the plunger rod position sensor, indicative of the plunger rod being in a known position, such as in the retracted plunger rod position, such as a fully retracted position. The processing unit may be configured to determine the position of the plunger rod based on the first plunger rod position sensor signal, e.g. the tachometer signal, and the second plunger rod position sensor signal. The processing unit may be configured to determine the plunger rod position based on the tachometer signal and the retracted plunger rod position. For example, the processing unit may be configured to determine the plunger rod position based on the number of revolutions of the drive module since the plunger rod was in the retracted plunger rod position.

Adjusting the movement of the plunger rod may comprise decreasing the plunger rod speed.

Adjusting the movement of the plunger rod may comprise stopping the movement of the plunger rod.

Adjusting the movement of the plunger rod may comprise preventing movement of the plunger rod towards the retracted plunger rod position for a dwell time. Alternatively or additionally, adjusting the movement of the plunger rod may comprise maintaining the position of the plunger rod for a dwell time. Preventing retraction or movement towards the retracted plunger rod position may prevent back flow of medicament due to lowering of the pressure inside the cartridge.

Adjusting the movement of the plunger rod may comprise moving the plunger rod to the retracted plunger rod position. For example, the plunger rod may be moved to the retracted plunger rod position after the dwell time.

Adjusting the movement of the plunger rod may comprise gradually decreasing the plunger rod speed, stopping the plunger rod speed, preventing movement of the plunger rod towards the retracted plunger rod position, and moving the plunger rod to the retracted plunger rod position after the dwell time.

The movement of the plunger rod may be readjusted after adjusting the movement of the plunger rod. The processing unit may be configured to control the drive module to readjust the movement of the plunger rod after adjusting the movement of the plunger rod. For example, the movement of the plunger rod may be readjusted after adjusting the movement of the plunger rod if the resistance against movement of the plunger rod is below the high resistance threshold. The processing unit may be configured to control the drive module to readjust the movement of the plunger rod after adjusting the movement of the plunger rod, if the resistance signal is indicative of resistance against movement of the plunger rod below the high resistance threshold. Readjusting the movement of the plunger rod may comprise increasing the plunger rod speed. The plunger rod speed may be varied. For example, the plunger rod speed may be based on the plunger rod position. The plunger rod speed may be a first plunger rod speed when the plunger rod position is between the retracted plunger rod position and a fourth plunger rod position. The plunger rod speed may be a second plunger rod speed when the plunger rod position is between a fifth plunger rod position and the extended plunger rod position. The second plunger rod speed may be lower than the first plunger rod speed. Alternatively, the second plunger rod speed may be higher than the first plunger rod speed. The processing unit may be configured to determine the plunger rod speed, e.g. based on the plunger rod position.

The fourth plunger rod position may be the first plunger rod position. The fifth plunger rod position may be the second plunger rod position. The first plunger rod position and the second plunger rod position may be the same plunger rod position. The fourth plunger rod position and the fifth plunger rod position may be the same plunger rod position.

The cartridge, such as the cartridge configured to be received by the auto injector, such as by the cartridge receiver of the auto injector, may have a cartridge outlet at a first cartridge end. The cartridge may comprise a cartridge back face, e.g. at the second cartridge end, such as opposite the cartridge outlet. The cartridge back face may comprise a cartridge back end opening. The cartridge back end opening may provide access for a plunger rod, such as the plunger rod of the auto injector, to the first stopper.

The cartridge compartment may contain a medicament. The cartridge outlet may be configured for fluid communication with the cartridge compartment, e.g. at the first cartridge end. The cartridge may be configured to expel medicament through the cartridge outlet. The cartridge outlet may be configured to be coupled with a needle, such as a hypodermic needle, to provide the medicament to be expelled through the needle.

The first stopper of the cartridge may be movable inside the cartridge compartment. The cartridge may comprise a second stopper movable inside the cartridge compartment. The second stopper may be between the first stopper and the cartridge outlet. The cartridge may comprise a third stopper movable inside the cartridge compartment. The third stopper may be between the second stopper and the cartridge outlet. The first stopper, the second stopper, and/or the third stopper may be movable inside the cartridge compartment towards the cartridge outlet, e.g. in a first stopper direction, such as towards a first cartridge end. For example, the medicament may be expelled through the cartridge outlet upon movement of the first stopper, the second stopper, and/or the third stopper, e.g. in the first stopper direction and/or towards the cartridge outlet.

The cartridge may be a dual chamber cartridge. The cartridge compartment may have a first cartridge subcompartment and a second cartridge subcompartment. The first cartridge subcompartment may be between the first stopper and the second stopper. The second cartridge subcompartment may be between the second stopper and the cartridge outlet and/or the third stopper.

The first cartridge subcompartment may contain a first medicament component of the medicament. The second cartridge subcompartment may contain a second medicament component of the medicament. Each of the first medicament component and/or second medicament component may be a powder composition, a fluid, a liquid, a gel, a gas, and/or any combination thereof. The first medicament component and/or the second medicament component may be solute, such as a powder composition. The first medicament component and/or the second medicament component may be a solvent, such as a fluid composition, such as a liquid composition. The second medicament component may be a powder composition and the first medicament component may be a fluid composition, e.g. water or ethanol or saline solution or buffer solution or preservative solution. The second medicament component may be a solute. The first medicament component may be a solvent. It is envisaged that the medicament may be any medicament being injectable via a hypodermic needle, for example after reconstitution of the medicament. The medicament may be a growth hormone. The medicament may be human growth hormone. The medicament may be a depot version, such as a long-acting version, of human growth hormone. The second medicament component may be a powder composition of human growth hormone. The cartridge may have a bypass section, e.g. for providing fluid communication between the first cartridge subcompartment and the second cartridge subcompartment, e.g. when the second stopper is positioned in the bypass section. The cartridge may have a plurality of bypass sections providing fluid communication between neighbouring cartridge subcompartments, e.g. when a stopper separating the neighbouring cartridge subcompartment is positioned in the respective bypass section. The disclosed auto injector may be a reusable auto injector. A reusable auto injector may be especially useful when the cartridge comprises a plurality of subcompartments. For example an auto injector for a multi compartment or multi chamber cartridge may be more advanced, and therefore it may be beneficial to allow the auto injector to be used more than one time. For example, the auto injector may provide automated processes for mixing medicament components, such as for mixing medicament components initially provided in different subcompartments of the cartridge.

It is envisaged that any embodiments or elements as described in connection with any one aspect may be used with any other aspects or embodiments, mutatis mutandis.

BRIEF DESCRIPTION OF THE DRAWINGS

The above and other features and advantages of the present invention will become readily apparent to those skilled in the art by the following detailed description of exemplary embodiments thereof with reference to the attached drawings, in which:

FIG. 1 schematically illustrates an exemplary auto injector;
FIG. 2 schematically illustrates an exemplary auto injector with a cartridge.

DETAILED DESCRIPTION

Figure 3:
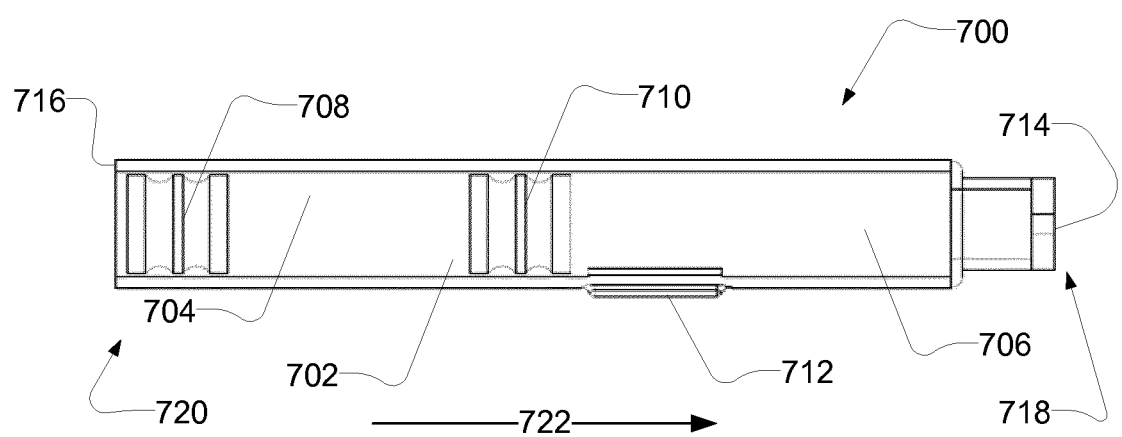
FIG. 3 schematically illustrates an exemplary cartridge.

Various embodiments are described hereinafter with reference to the figures. Like reference numerals refer to like elements throughout the description. Like elements may, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout, the same reference numerals are used for identical or corresponding parts.

FIG. 1 illustrates an exemplary auto injector 4. The auto injector 4 may be configured for administering a medicament. The auto injector 4 may be an electronic auto injector. The auto injector 4 comprises a housing 6. The auto injector 4 comprises a cartridge receiver 300. The cartridge receiver is configured to receive a cartridge and/or a cartridge assembly comprising a cartridge. The cartridge may contain the medicament. The cartridge receiver 300 has a cartridge receiver opening 301. The cartridge receiver 300 is configured to receive the cartridge and/or the cartridge assembly through the cartridge receiver opening 301 in a cartridge receiving direction 304 along a longitudinal axis L.

The auto injector 4 may comprise a user interface 1100, as illustrated. The auto injector 4 comprises a trigger member, such as a contact member 1102. The contact member 1102 may be configured to be pressed against an injection site. The contact member 1102 may be movable in the cartridge receiving direction 304, relative to the housing, if pressed against the injection site. The contact member 1102 may be part of the user interface 1100.

The user interface 1100 may comprise a first input member 1108 as illustrated, e.g. a button. The first input member 1108 may provide for a user input from a user. For example, the first input member 1108 may be used for receiving a push from a user to proceed to a next step.

The user interface 1100 may comprise a first output member 1110 as illustrated, e.g. a plurality of LEDs. The first output member 1110 may provide for a user output to a user. The user interface 1100 may comprise a second output member (not shown), e.g. a speaker. The second output member may be configured to provide audible output to the user. For example, the first output member 1110 and/or the second output member may be used to indicate a step in the procedure to the user and/or to indicate an error message.

FIG. 2 illustrates an exemplary system 2. The system 2 comprises an auto injector 4, as described in relation to FIG. 1, and an exemplary cartridge 700 received in the cartridge receiver 300. The cartridge 700 comprises a first stopper (not shown). The cartridge 700 is shown with a needle cover 908. The needle cover 908 may extend out of the contact member 1102, as shown, to allow removal of the needle cover 908 from the cartridge 700.

FIG. 3 schematically illustrates an exemplary cartridge 700, such as a cartridge 700 being configured to be received in the cartridge receiver of an auto injector, such as the auto injector described in relation to previous figures.

The cartridge 700 comprises a cartridge compartment 702. The cartridge compartment 702 may be configured for containing a medicament. The cartridge 700 has a first end 718 and a second end 720. The cartridge 700 comprises a cartridge outlet 714 at a first cartridge end 718. The cartridge may be configured to expel medicament through the cartridge outlet 714.

The cartridge comprises a first stopper 708 movable inside the cartridge compartment 702, e.g. in a first stopper direction 722, e.g. towards the first cartridge end 718. For example, the medicament may be expelled through the cartridge outlet 714 upon movement of the first stopper 708 in the first stopper direction 722. The cartridge 700 comprises a cartridge back face 716 at the second cartridge end 720. The cartridge back face 716 comprises a cartridge back end opening for providing access to the first stopper 708 for a plunger rod.

As illustrated, the cartridge 700 may be a dual chamber cartridge. Hence, the cartridge 700 comprises a second stopper 710 movable inside the cartridge compartment 702, e.g. in the first stopper direction 722, e.g. towards the first cartridge end 718. The cartridge compartment 702 comprises a first cartridge subcompartment 704 and a second cartridge subcompartment 706. The first cartridge subcompartment 704 is between the first stopper 708 and the second stopper 710. The first cartridge subcompartment 704 may comprise a liquid, such as sterile water or a buffer solution. The second cartridge subcompartment 706 is between the second stopper 710 and the cartridge outlet 714. The second cartridge subcompartment 706 may comprise a medicament, such as a dry medicament, such as a medicament dried by lyophilization. The cartridge 700 comprises a bypass section 712 for providing fluid communication between the first cartridge subcompartment 704 and the second cartridge subcompartment 706. The bypass section 712 provides fluid communication between the first cartridge subcompartment 704 and the second cartridge subcompartment 706 when the second stopper 710 is positioned in the bypass section 712.

Figure 4:
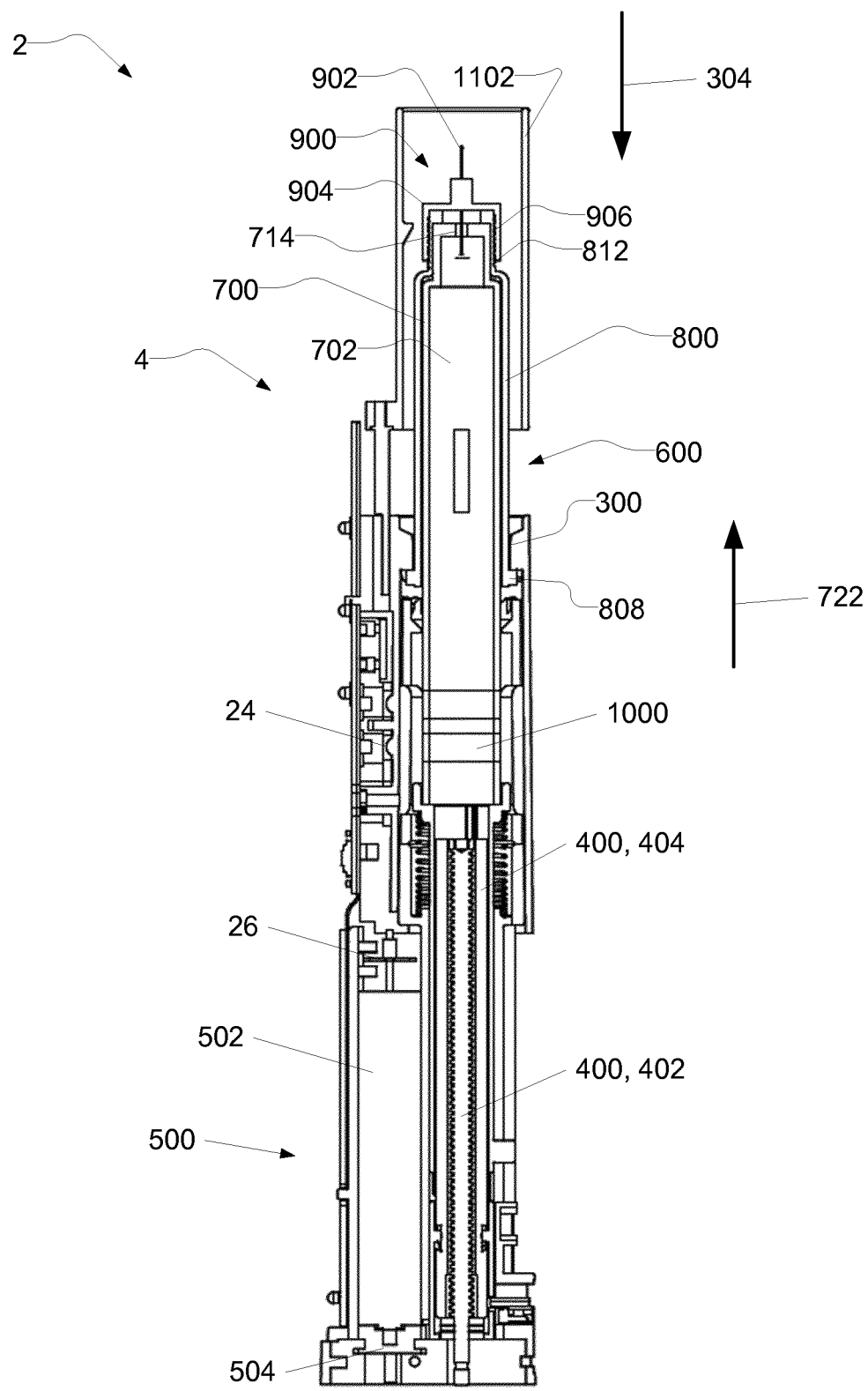
FIG. 4 schematically illustrates an exemplary auto injector with a cartridge.

FIG. 4 illustrates an exemplary system 2. The system 2 comprises an auto injector 4, as described, for example, in relation to FIG. 1, and an exemplary cartridge assembly 600. The cartridge assembly 600 comprises a cartridge 700 with a cartridge compartment 702, a needle assembly 900, and an optional cartridge code feature 1000. The cartridge assembly 600 is, in the illustrated example, received in the auto injector 4.

The cartridge assembly 600 comprises a cartridge holder 800. The cartridge holder is configured for retention of the cartridge 700 in the cartridge receiver 300 of the auto injector 4. The cartridge holder 800 comprises a cartridge retention member 808. The cartridge retention member engages with the cartridge receiver 300 for reception of the cartridge 700 and the cartridge assembly 600 in the cartridge receiver.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700. The cartridge outlet 714 may be blocked by a resilient sealing being penetrated by the needle 902, when the needle assembly 900 is attached to the cartridge 700.

The auto injector 4 comprises an optional code sensor 24 configured to read the cartridge code feature 1000. When the cartridge assembly 600 is inserted, as shown, the cartridge code feature 1000 is lined up with the code sensor 24.

The auto injector 4 comprises a plunger rod 400. The plunger rod 400 is configured to advance a first stopper of the cartridge 700. The plunger rod 400 comprises an outer plunger rod 404 with an inner thread, and an inner plunger rod 402 with an outer thread. The thread of the inner plunger rod 402 is in engagement with the thread of the outer plunger rod 404. The outer plunger rod 404 is prevented from rotating relative to the housing of the auto injector. The movement of the plunger rod 400 comprises rotation of the inner plunger rod 402. The rotation of the inner plunger rod 402 results in translational movement of the outer plunger rod 404, due to the outer plunger rod 404 being rotationally restricted. The outer plunger rod 404, when moved translationally in the first stopper direction 722, is configured to abut the first stopper of the cartridge 700, and to move the first stopper in the first stopper direction 722.

The drive module 500 is coupled to actuate the plunger rod 400. The drive module 500 is electrically connected to a battery for receiving electrical power. The drive module 500 comprises a motor 502, such as an electro-mechanical motor, such as a DC motor. The drive module 500 comprises a transmission 504 for coupling the motor 502 to the inner plunger rod 402 of the plunger rod 400.

Although the example shown comprises a motor 502, which may be an electro-mechanical motor, it will be readily understood that the auto injector 4 may be realised having an alternative drive module, such as comprising a solenoid motor, a shape memory metal engine, an arrangement of springs and/or a pressurized gas configured to actuate the plunger rod 400.

The auto injector 4 comprises a plunger rod position sensor 26. The plunger rod position sensor 26 is configured to detect the position of the plunger rod 400. In the illustrated example, the plunger rod position sensor 26 comprises a tachometer configured to count/detect the revolutions of the motor 502. Thus, the position of the plunger rod 400 may be determined. The plunger rod position sensor 26 may, based on the detection of the position of the plunger rod 400, detect the expelling of medicament and/or air in the cartridge compartment. The position of the plunger rod 400 is indicative of the position of the first stopper 708 of the cartridge 700.

Figure 5:
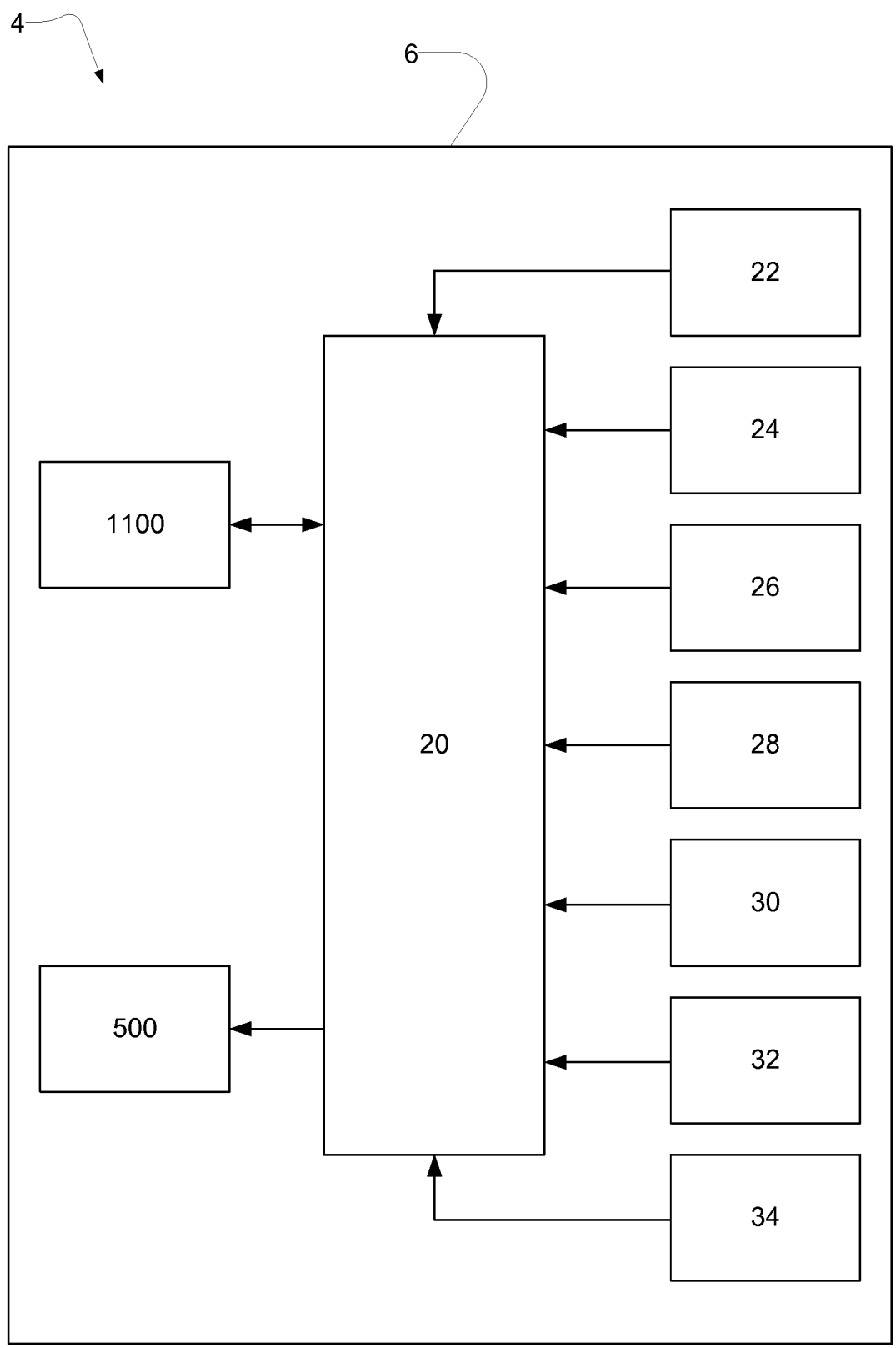
FIG. 5 shows a block diagram of an exemplary auto injector.

FIG. 5 shows a block diagram of an exemplary auto injector 4. The auto injector 4 comprises a plurality of sensors 22, 24, 26, 28, 30, 32, 34, a processing unit 20, a drive module 500, and a user interface 1100. The sensors 22, 24, 26, 28, 30, 32, 34 are coupled to the processing unit 20. The user interface 1100 is coupled to the processing unit 20. The processing unit is coupled to the drive module 500.

The processing unit 20 receives signals from the sensors 22, 24, 26, 28, 30, 32, 34 and the user interface 1100. The processing unit 20 is configured to control the drive module 500. The processing unit 20 may control the drive module 500 based on one or more of the received signals from the sensors 22, 24, 26, 28, 30, 32, 34 and the user interface 1100.

The auto injector 4 comprises an orientation sensor 22. The orientation sensor 22 is configured to provide an orientation signal indicative of the orientation of a cartridge received in the auto injector 4. For example, the orientation sensor 22 may be configured to detect the orientation of the auto injector 4. The orientation of the cartridge may be determined based on the orientation of the auto injector 4. The orientation sensor 22 may be configured to detect the direction of gravity. For example, the orientation sensor 22 may comprise an accelerometer.

The processing unit 20 is coupled to the orientation sensor 22. The processing unit 20 is configured to receive the orientation signal. The processing unit 20 may determine the orientation of the cartridge based on the orientation signal. The processing unit 20 may control the drive module 500 based on the orientation signal. For example, the processing unit 20 may be configured to control the drive module 500 to move a plunger rod based on the orientation signal. For example, the processing unit 20 may be configured to control the drive module 500 to move the plunger rod towards an extended plunger rod position only if the cartridge outlet is pointing upwards. Alternatively or additionally, the processing unit 20 may provide user output via the user interface 1100 based on the orientation signal.

The auto injector 4 comprises a code sensor 24. The code sensor 24 is configured to read a cartridge code feature. The code sensor 24 is configured to provide a code signal indicative of a cartridge code feature. For example, the code sensor may be configured to read/detect a colour code.

The processing unit 20 is coupled to the code sensor 24. The processing unit 20 is configured to receive the code signal. The processing unit 20 may determine the cartridge code feature of the cartridge assembly based on the code signal. The processing unit 20 may be configured to determine a first plunger rod position and/or a second plunger rod position based on the code signal. The processing unit 20 may control the drive module 500 based on the code signal. For example, the processing unit 20 may be configured to control the drive module 500 to move the plunger rod towards the extended plunger rod position based on the code signal. Alternatively or additionally, the processing unit 20 may provide user output via the user interface 1100 based on the code signal.

The auto injector 4 comprises a plunger rod position sensor 26. The plunger rod position sensor 26 is configured to detect the position of the plunger rod of the auto injector 4, and provide a plunger rod position sensor signal indicative of the position of the plunger rod. The plunger rod position sensor 26 may comprise a tachometer coupled to the drive module 500.

The processing unit 20 is coupled to the plunger rod position sensor 26. The processing unit 20 is configured to receive the plunger rod position sensor signal. The processing unit 20 may determine the position of the plunger rod based on the plunger rod position sensor signal. The processing unit 20 may control the drive module 500 based on the plunger rod position sensor signal. For example, the processing unit 20 may be configured to control the drive module 500 to start, stop or continue movement of the plunger rod based on the plunger rod position sensor signal. For example, the processing unit 20 may be configured to determine a plunger rod position based on the plunger rod position sensor signal. Alternatively or additionally, the processing unit 20 may provide user output via the user interface 1100 based on the plunger rod position sensor signal.

The processing unit 20 is coupled to the cartridge sensor 28. The processing unit 20 is configured to receive the cartridge sensor signal. The processing unit 20 may control the drive module 500 based on the cartridge sensor signal. For example, the processing unit 20 may be configured to control the drive module 500 to start movement of the plunger rod if a cartridge assembly is received, and/or only if a cartridge assembly is received. Alternatively or additionally, the processing unit 20 may provide user output via the user interface 1100 based on the cartridge sensor signal.

The code sensor 24 and the cartridge sensor 28 may be the same sensor, e.g. the code sensor 24 may be configured to detect reception of a cartridge assembly and subsequently read the cartridge code feature.

The auto injector 4 comprises a needle sensor 30. The needle sensor 30 is configured to detect a needle, and/or a needle assembly, and/or a needle cover of a needle assembly, of the cartridge assembly, when the cartridge assembly is received in the auto injector 4. The needle sensor 30 provides a needle signal indicative of the presence of a needle, and/or a needle assembly, and/or a needle cover of a needle assembly, of the cartridge assembly.

The processing unit 20 is coupled to the needle sensor 30. The processing unit 20 is configured to receive the needle signal. The processing unit 20 may control the drive module 500 based on the needle signal. For example, the processing unit 20 may be configured to control the drive module 500 to start movement of the plunger rod only if a needle is present, and/or only if a needle cover is not present, such as removed. Detection of a needle cover may be indicative of a needle being present. The processing unit 20 may be configured to control the drive module 500 to start only if a needle cover has been detected, and afterwards removed. Alternatively or additionally, the processing unit 20 may provide user output via the user interface 1100 based on the needle signal.

The auto injector 4 comprises a temperature sensor 32. The temperature sensor 32 is configured to detect a temperature, such as a temperature of the auto injector and/or of the cartridge and/or of the medicament. The temperature sensor 32 is configured to provide a temperature signal indicative of the temperature.

The processing unit 20 is coupled to the temperature sensor 32. The processing unit 20 is configured to receive the temperature signal. The processing unit 20 may be configured to determine the temperature, such as the temperature of the auto injector and/or of the cartridge and/or of the medicament based on the temperature signal. The processing unit 20 may control the drive module 500 based on the temperature signal. For example, the processing unit 20 may be configured to control the drive module 500 to move the plunger rod towards the extended plunger rod position based on the temperature signal. Alternatively or additionally, the processing unit 20 may provide user output via the user interface 1100 based on the temperature signal.

The auto injector 4 comprises a resistance sensor 34. The resistance sensor 34 is configured to detect resistance against movement of the plunger rod of the auto injector 4. The resistance sensor 34 may be configured to detect resistance against movement of the plunger rod based on measurements of the drive module 500. For example, the resistance sensor 34 may be configured to detect the electrical current of a motor of the drive module 500. For example, the resistance sensor 34 may be configured to determine the electrical current through the drive module. Alternatively or additionally, the resistance sensor 34 may be configured to measure pressure and/or force applied to a plunger rod front end of the plunger rod. The resistance sensor 34 is configured to provide a resistance signal indicative of resistance against movement of the plunger rod.

The processing unit 20 is coupled to the resistance sensor 34. The processing unit 20 is configured to receive the resistance signal. The processing unit 20 may be configured to determine the resistance against movement of the plunger rod based on the resistance signal. The processing unit 20 may control the drive module 500 based on the resistance signal. For example, the processing unit 20 may be configured to control the drive module 500 to adjust movement of the plunger rod based on the resistance signal. For example, the processing unit 20 may be configured to control the drive module 500 to start, stop or continue movement of the plunger rod based on the resistance signal.

Movement of the plunger rod results in a plunger rod speed. The processing unit 20 may be configured to determine the plunger rod speed. The processing unit 20 may be configured to control the drive module 500 to adjust, such as readjust, the movement of the plunger rod, if the resistance signal is indicative of resistance against movement of the plunger rod above a high resistance threshold. The processing unit 20 may further be configured to control the drive module 500 to adjust, such as readjust, the movement of the plunger rod, wherein adjusting the movement of the plunger rod may comprise increasing or decreasing the plunger rod speed. Alternatively or additionally, the processing unit 20 may provide user output via the user interface 1100 based on the resistance signal. The high resistance threshold may be based on the plunger rod position. The processing unit 20 may be configured to determine the high resistance threshold, e.g. based on the plunger rod position. The processing unit 20 may be configured to determine the high resistance threshold based on the plunger rod position sensor signal, e.g. received from the plunger rod position sensor 26.

The auto injector 4 is illustrated comprising all of the above mentioned sensors. However, alternatively, the auto injector may comprise only one or any combination of one or more of the above mentioned sensors.

The auto injector comprises a user interface 1100. The user interface 1100 may comprise one or more input members, e.g. a first input member, for receiving a user input. The user interface is configured to provide a user input signal indicative of the received user input.

The processing unit 20 is coupled to the user interface 1100. The processing unit 20 is configured to receive the user input signal. The processing unit 20 may control the drive module 500 based on the user input signal. For example, the processing unit 20 may be configured to control the drive module 500 to move the plunger rod towards the extended plunger rod position based on the user input signal.

The auto injector comprises a housing 6 accommodating the sensors 22, 24, 26, 28, 30, 32, 34, processing unit 20, user interface 1100 and drive module 500.

Figure 6:
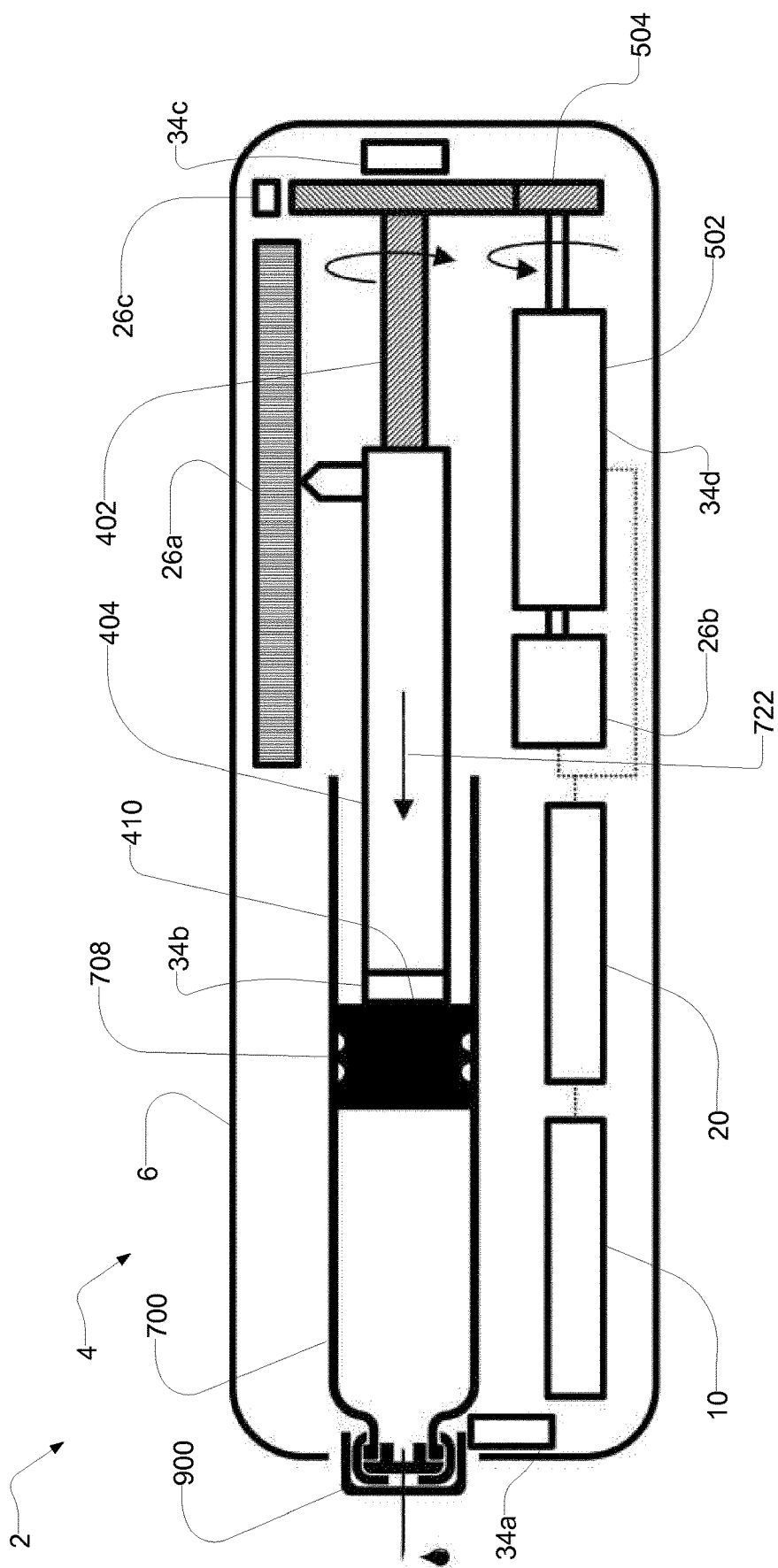
FIG. 6 schematically illustrates an exemplary auto injector.

FIG. 6 schematically illustrates a system 2 comprising an exemplary auto injector 4 with an inserted cartridge assembly comprising a cartridge 700 and a needle assembly 900.

The auto injector 4 as shown in FIG. 6 illustrates different ways of implementing sensing of plunger rod position and resistance against movement of the plunger rod.

The plunger rod comprises an outer plunger rod 404 with an inner thread, and an inner plunger rod 402 with an outer thread. The thread of the inner plunger rod 402 is in engagement with the thread of the outer plunger rod 404. The outer plunger rod 404 is prevented from rotating relative to the housing 6 of the auto injector 4. Rotation of the inner plunger rod 402 results in translational movement of the outer plunger rod 404, due to the outer plunger rod 404 being rotationally restricted. The outer plunger rod 404, when moved translationally in the first stopper direction 722, is configured to abut the first stopper 708 of the cartridge 700, and to move the first stopper in the first stopper direction 722. The plunger rod front end 410 is configured to abut the first stopper 708.

A motor 502 is coupled to drive the plunger rod via a transmission 504. The motor 502 rotates a first part of the transmission 504, which rotates a second part of the transmission 504, which is coupled to rotate the inner plunger rod 402.

The motor 502 is controlled by a processing unit 20. The auto injector 4, such as the motor 502 and/or the processing unit 20, is powered by a battery 10, such as a rechargeable battery.

Position of the plunger rod, such as the position of the outer plunger rod 404 and/or the position of the plunger rod front end 410, may be determined by one or more position sensors 26a, 26b, 26c. For example, as illustrated, the plunger rod position may be determined by a position sensor 26a configured to sense position through a linear sensor coupled to the plunger rod, such as the outer plunger rod 404. Alternatively or additionally, as also illustrated, the plunger rod position may be determined by a position sensor 26b, such as a tachometer, configured to count/detect the revolutions of the motor 502. Alternatively or additionally, as also illustrated, the plunger rod position may be determined by a position sensor 26c, such as a tachometer, configured to count/detect the revolutions of the transmission 504 and/or a part of the transmission 504.

Resistance against movement of the plunger rod may be determined by one or more resistance sensors 34a, 34b, 34c, 34d. For example, as illustrated the resistance against movement of the plunger rod may be determined by a resistance sensor, such as a force sensor, 34a positioned in front of the cartridge 700, when the plunger rod advances the first stopper 708, the cartridge will press against the sensor 34a. Alternatively or additionally, as also illustrated, the resistance against movement of the plunger rod may be determined by a resistance sensor, such as a force sensor, 34b positioned on the plunger rod front end 410. Alternatively or additionally, as also illustrated, the resistance against movement of the plunger rod may be determined by a resistance sensor, such as a force sensor, 34c positioned to sense the reaction force from the plunger rod on first stopper 708, e.g. the sensor 34c may be positioned behind the inner plunger rod 402. Alternatively or additionally, as also illustrated, the resistance against movement of the plunger rod may be determined by a resistance sensor 34d configured to measure/detect the amount of current and/or power drawn by the motor 502.

Figure 7:
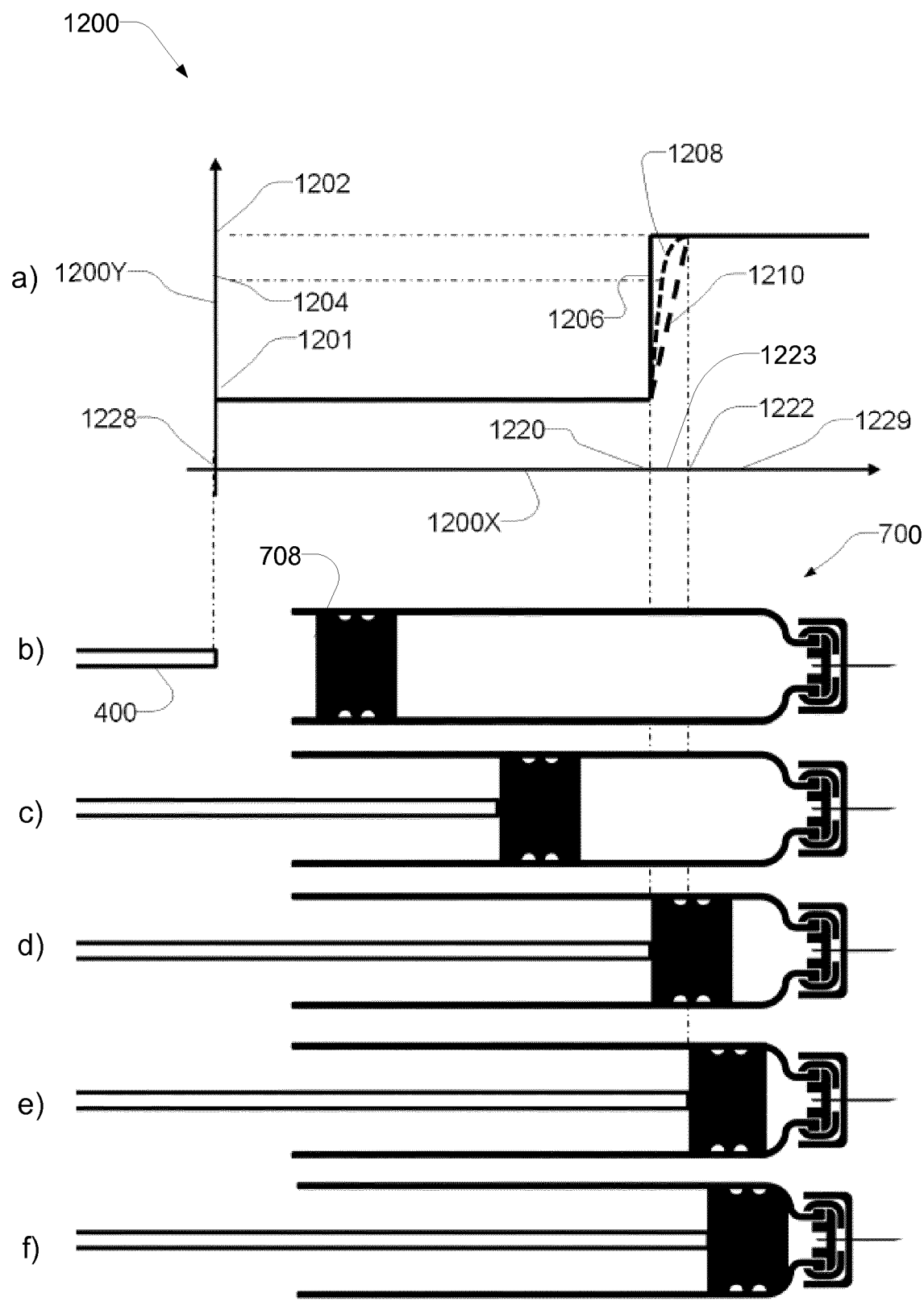
FIG. 7 shows an exemplary graph of resistance threshold vs. plunger position.

FIG. 7a shows a resistance graph 1200 illustrating a high resistance threshold depending on stopper position/plunger rod position, such as the high resistance threshold and the plunger rod position as described in relation to previous figures, and/or the stopper position associated with the plunger rod position as described in relation to previous figures. A plunger rod 400 is configured to move the first stopper 708, thus the position of the first stopper 708 is determined by the position of the plunger rod 400. Therefore, the position of the first stopper 708 may be corresponding to a position of the plunger rod 400. The plunger rod position may designate a plunger rod front end, such as the part of the plunger rod making contact with the first stopper 708.

The resistance graph 1200 has a first axis 1200X indicating stopper position/plunger rod position and a second axis 1200Y indicating resistance. Solid and dashed lines illustrate different examples of how the high resistance threshold may vary depending on stopper position/plunger rod position.

FIGS. 7b-f illustrates a plunger rod 400 and a cartridge 700 with a first stopper 708 in situations of corresponding exemplary plunger rod positions explained in the following. FIG. 7b shows the plunger rod 400 being in a retracted plunger rod position 1228. FIG. 7c shows the plunger rod 400 being in a position between the retracted plunger rod position 1228 and a first plunger rod position 1220. The first stopper 708 has been moved accordingly. FIG. 7d shows the plunger rod 400 being in the first plunger rod position 1220. The first stopper 708 has been moved accordingly to a first stopper position. FIG. 7e shows the plunger rod 400 being in a second plunger rod position 1222. The first stopper 708 has been moved accordingly to a second stopper position. FIG. 7f shows the plunger rod 400 being in a position between the second plunger rod position 1222 and an extended plunger rod position 1229. The first stopper 708 has been moved accordingly. The plunger rod position illustrated in FIG. 7f may be the extended plunger rod position 1229.

As illustrated by the graph in FIG. 7a, the high resistance threshold may be a first high resistance threshold 1201 when the plunger rod position is between the retracted plunger rod position 1228 and the first plunger rod position 1220. The high resistance threshold may be a second high resistance threshold 1202 when the plunger rod position is between the second plunger rod position 1222 and the extended plunger rod position 1229.

The second high resistance threshold 1202 may be higher than the first high resistance threshold 1201. For example, the first high resistance threshold 1201 may be between 50-80 N, such as 50 N, 55 N, 60 N, 65 N, 70 N, 75 N, or 80 N. For example, the second high resistance threshold 1202 may be between 70-100 N, such as between 75-85 N, or such as between 80-90 N, or such as 70 N, 75 N, 80 N, 85 N, or 90 N.

As illustrated by the solid line, the high resistance threshold may be the second high resistance threshold 1202 when the plunger rod position is between the first plunger rod position 1220 and the extended plunger rod position 1229. Alternatively or additionally, the high resistance threshold may be a third high resistance threshold 1204 when the plunger rod position is between the first plunger rod position 1220 and the second plunger rod position 1222, such as when the plunger rod position is at a third plunger rod position 1223. The third high resistance threshold 1204 may be higher than the first high resistance threshold 1201. The third high resistance threshold 1204 may be lower than the second high resistance threshold 1202.

The high resistance threshold may be increasing as a function of the plunger rod position. For example, as illustrated, the high resistance threshold may be increasing as the plunger rod is moved from the first plunger rod position 1220 to the second plunger rod position 1222. The solid and dashed lines illustrate exemplary ways the high resistance threshold may increase as the plunger rod is moved from the first plunger rod position 1220 to the second plunger rod position 1222. A first slope 1206 illustrates a step-change increase. A second slope 1208 illustrates a non-linear increase. A third slope 1210 illustrates a linear increase.

Figure 8:
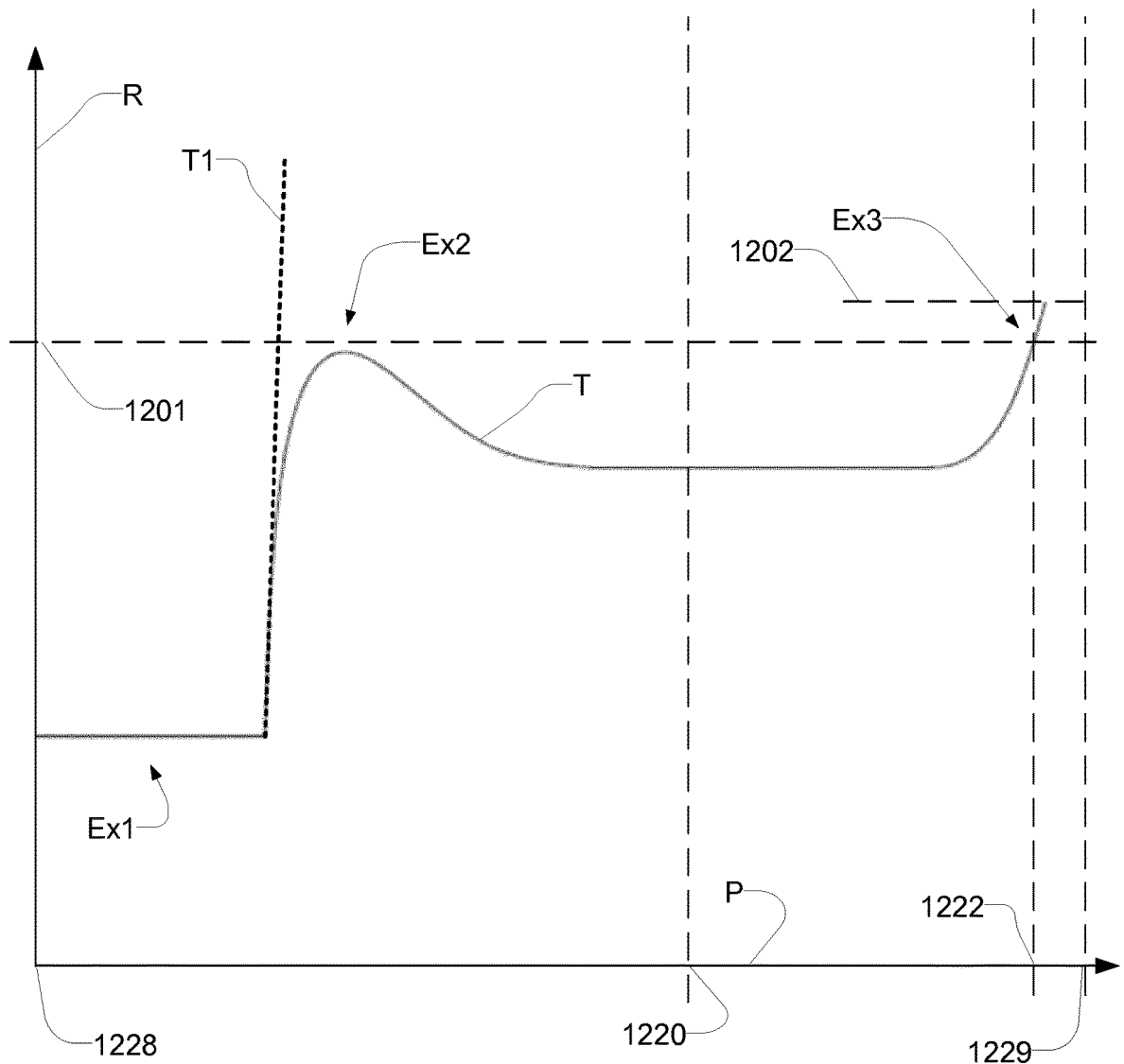
FIG. 8 shows an exemplary graph of resistance vs plunger position.

FIG. 8 shows an exemplary trace T of resistance R against movement of the plunger rod dependent on the position of the plunger rod P. The plunger rod is moved from a retracted position 1228 to an extended position 1229. In the beginning of the movement, the resistance against movement of the plunger rod is constant Ex1, e.g. the plunger rod does not yet push a stopper. Afterwards, a plunger rod front end of the plunger rod abuts a first stopper of the cartridge, and the resistance against movement of the plunger rod increases Ex2. The increased resistance is caused by the resistance against movement of the first stopper, e.g. due to frictional force. The resistance may decrease slightly after the first stopper has started moving, as illustrated. When the plunger rod approaches the extended plunger rod position 1229, the resistance may increase again Ex3, e.g. due to the first stopper approaching an end of the cartridge.

The trace T is an example of resistance against plunger rod movement when the cartridge received is a new and/or unused and/or normal cartridge. Other situations, such as situations wherein the cartridge received is apparently flawed, are exemplified by additional exemplary trace, T1.

Trace T1 illustrates an exemplary situation wherein the resistance against movement increases above a first high resistance threshold 1201, e.g. before the plunger rod position has passed the first plunger rod position 1220. Such situation may for example indicate that the first stopper is blocked from moving, e.g. the cartridge may be flawed. Following such situation, the plunger rod may be retracted to the retracted position and an error message may be provided through a user interface.

At a certain plunger rod position, such as the first plunger rod position 1220, the high resistance threshold may be changed, e.g. in order to allow for a higher resistance before aborting the movement of the plunger rod. As illustrated, at the end of the forward movement of the plunger rod, the resistance R increases, e.g. at the second plunger rod position 1222, to a resistance above the first high resistance threshold 1201. However, since the high resistance threshold at the second plunger rod position is a second high resistance threshold 1202, the movement of the plunger rod is continued. Eventually, as illustrated, the resistance against movement may reach the second high resistance threshold 1202, e.g. between the second plunger rod position and the extended plunger rod position 1229, and the movement of the plunger rod may be stopped.

The thresholds, such as the first high resistance threshold 1201 and/or the second high resistance threshold 1202 may be individually determined for the cartridge received. For example, a processing unit may be configured to determine one or more of the thresholds, based on a cartridge code feature of the cartridge and/or cartridge assembly received.

Figure 9:
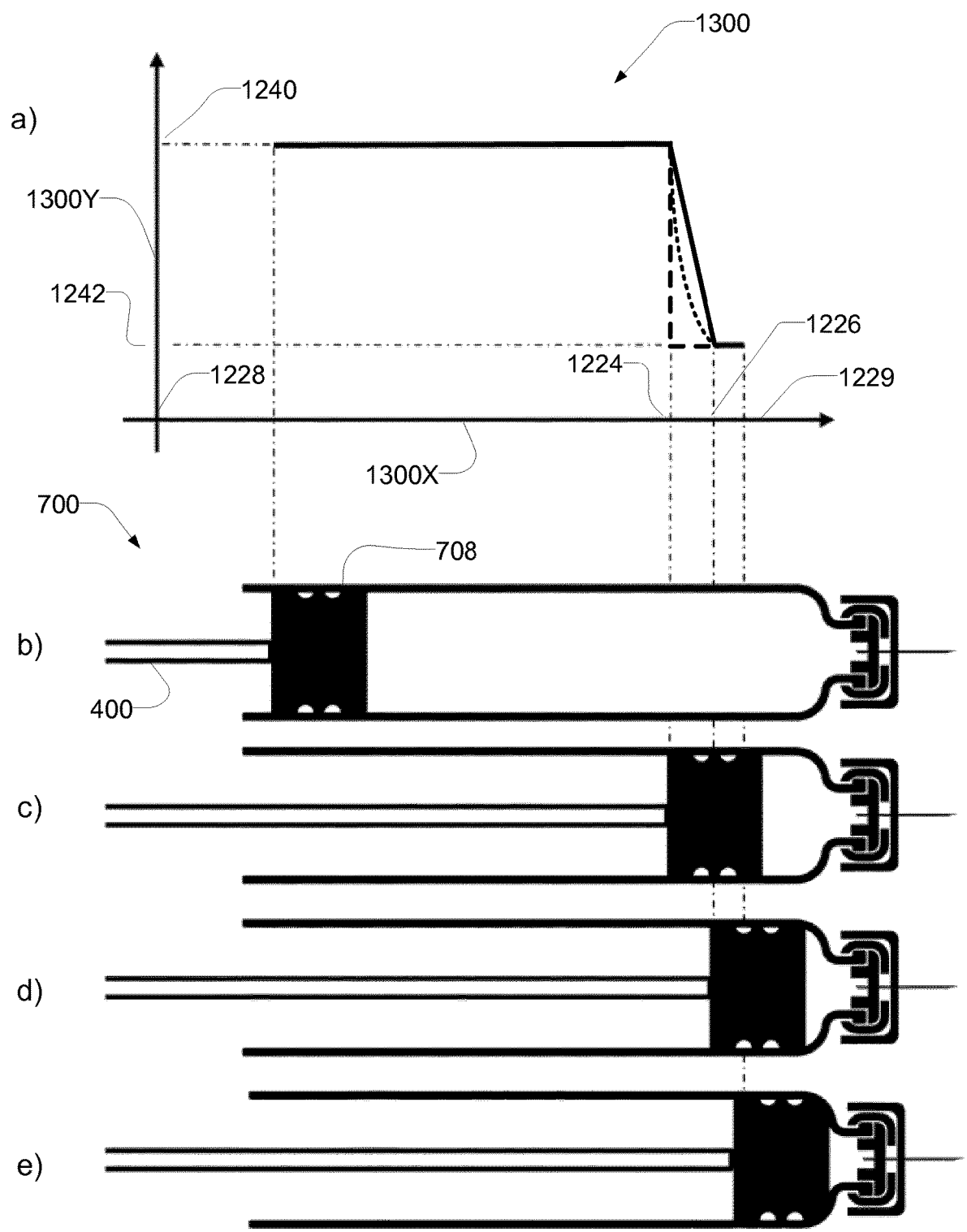
FIG. 9 shows an exemplary graph of plunger speed vs. plunger position.

FIG. 9a shows a speed graph 1300 illustrating a plunger rod speed depending on stopper position/plunger rod position, such as the plunger rod speed and the plunger rod position as described in relation to previous figures, and/or the stopper position associated with the plunger rod position as described in relation to previous figures. A plunger rod 400 is configured to move the first stopper 708, thus the position of the first stopper is determined by the position of the plunger rod 400. Therefore, the position of the first stopper may be corresponding to a position of the plunger rod 400. The plunger rod position may designate a plunger rod front end, such as the part of the plunger rod making contact with the first stopper 708.

The speed graph 1300 has a first axis 1300X indicating stopper position/plunger rod position and a second axis 1300Y indicating speed, such as plunger rod speed. Solid and dashed lines illustrate different examples of how plunger rod speed may vary depending on stopper position/plunger rod position.

FIGS. 9b-e illustrate a plunger rod 400 and a cartridge 700 with a first stopper 708 in situations of corresponding exemplary plunger rod positions explained in the following. FIG. 9b shows the plunger rod 400 being in a position between a retracted plunger rod position 1228 and a fourth plunger rod position 1224. FIG. 9c shows the plunger rod 400 being in the fourth plunger rod position 1224. The first stopper 708 has been moved accordingly to a fourth stopper position. FIG. 9d shows the plunger rod 400 being in a fifth plunger rod position 1226. The first stopper 708 has been moved accordingly to a fifth stopper position. FIG. 9e shows the plunger rod 400 being in a position between the fifth plunger rod position 1226 and an extended plunger rod position 1229. The first stopper 708 has been moved accordingly. The plunger rod position illustrated in FIG. 9e may be the extended plunger rod position 1229.

As illustrated by the graph in FIG. 9a, the plunger rod speed may be based on the plunger rod position. For example, the plunger rod speed may be a first plunger rod speed 1240 when the plunger rod position is between the retracted plunger rod position 1228 and the fourth plunger rod position 1224. The plunger rod speed may be a second plunger rod speed 1242 when the plunger rod position is between the fifth plunger rod position 1226 and the extended plunger rod position 1229. The second plunger rod speed 1242 may be lower than the first plunger rod speed 1240. Alternatively, the second plunger rod speed 1242 may be higher than the first plunger rod speed 1240 in order to effectively empty the cartridge.

A plunger rod position may coincide with another plunger rod position. For example, the fourth plunger rod position 1224 may be the first plunger rod position 1220 as mentioned in relation to FIG. 7. The fifth plunger rod position 1226 may be the second plunger rod position 1222 as mentioned in relation to FIG. 7.

The plunger rod speed may be decreasing as a function of the plunger rod position. For example, the plunger rod speed may be decreasing as the plunger rod is moved from the fourth plunger rod position 1224 to the fifth plunger rod position 1226. The solid line illustrates an exemplary linear decrease of the plunger rod speed as the plunger rod is moved from the fourth plunger rod position 1224 to the fifth plunger rod position 1226. Other examples may be non-linear decrease and step-change decrease as exemplified by the dashed lines.

Figure 10:
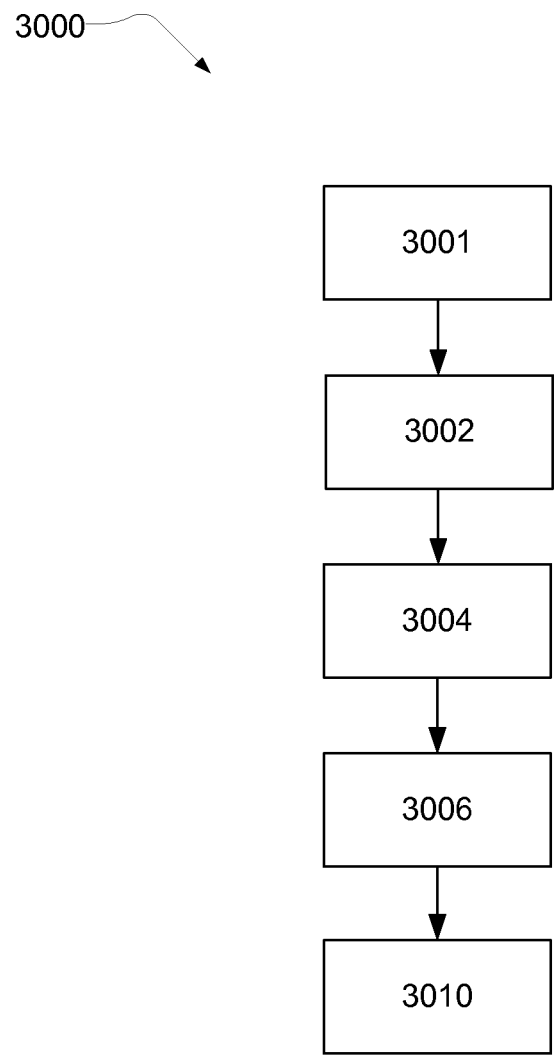
FIG. 10 shows a flow chart of an exemplary method.

FIG. 10 shows a flow chart of an exemplary method 3000 for operating and/or controlling an auto injector, such as the auto injector as described in relation to previous figures.

The method 3000 comprises receiving 3001 a cartridge comprising a first stopper; moving 3002 a plunger rod towards an extended plunger rod position; determining 3004 plunger rod position; receiving a resistance signal 3006; and adjusting 3010 the movement of the plunger rod.

Receiving 3001 the cartridge may comprise receiving the cartridge in a cartridge receiver of the auto injector.

Moving 3002 the plunger rod may comprise moving the plunger rod from a retracted plunger rod position. Moving 3002 the plunger rod may comprise moving the plunger rod in a first plunger rod direction.

Determining 3004 plunger rod position may be determined by a processing unit of the auto injector. Determining 3004 plunger rod position may be based on detection from a sensor, such as a plunger rod position sensor, e.g. comprising a tachometer.

Receiving a resistance signal 3006 may comprise receiving the resistance signal from a resistance sensor. The resistance signal may be indicative of resistance against movement of the plunger rod, such as movement towards the extended plunger rod position, such as movement in the first plunger rod direction.

Adjusting 3010 the movement may comprise stopping the movement of the plunger rod. Alternatively or additionally, adjusting 3010 the movement may comprise preventing movement of the plunger rod towards the retracted plunger rod position for a dwell time, e.g. in order to prevent back flow of medicament. Alternatively or additionally, adjusting 3010 the movement may comprise maintaining the position of the plunger rod for a dwell time, e.g. in order to prevent back flow of medicament. Alternatively or additionally, adjusting 3010 the movement may comprise moving the plunger rod to the retracted plunger rod position. Alternatively or additionally, adjusting 3010 the movement may comprise decreasing the plunger rod speed.

Adjusting 3010 the movement of the plunger rod may be based on the resistance signal. For example, the movement of the plunger rod may be adjusted such that the resistance is held below a high resistance threshold. Adjusting 3010 the movement of the plunger rod may comprise adjusting the movement of the plunger rod if the resistance signal is indicative of resistance against movement of the plunger rod above a high resistance threshold. The high resistance threshold may be based on the plunger rod position, e.g. the high resistance threshold may be a first high resistance threshold when the plunger rod position is within a one range, and a second high resistance threshold when the plunger rod position is within a second range.

Steps of the exemplary method 3000, e.g the steps of moving 3002 a plunger rod; determining 3004 plunger rod position; receiving a resistance signal 3006; and adjusting 3010 the movement of the plunger rod, may be controlled by a processing unit, such as the processing unit of the auto injector.

Figure 11:
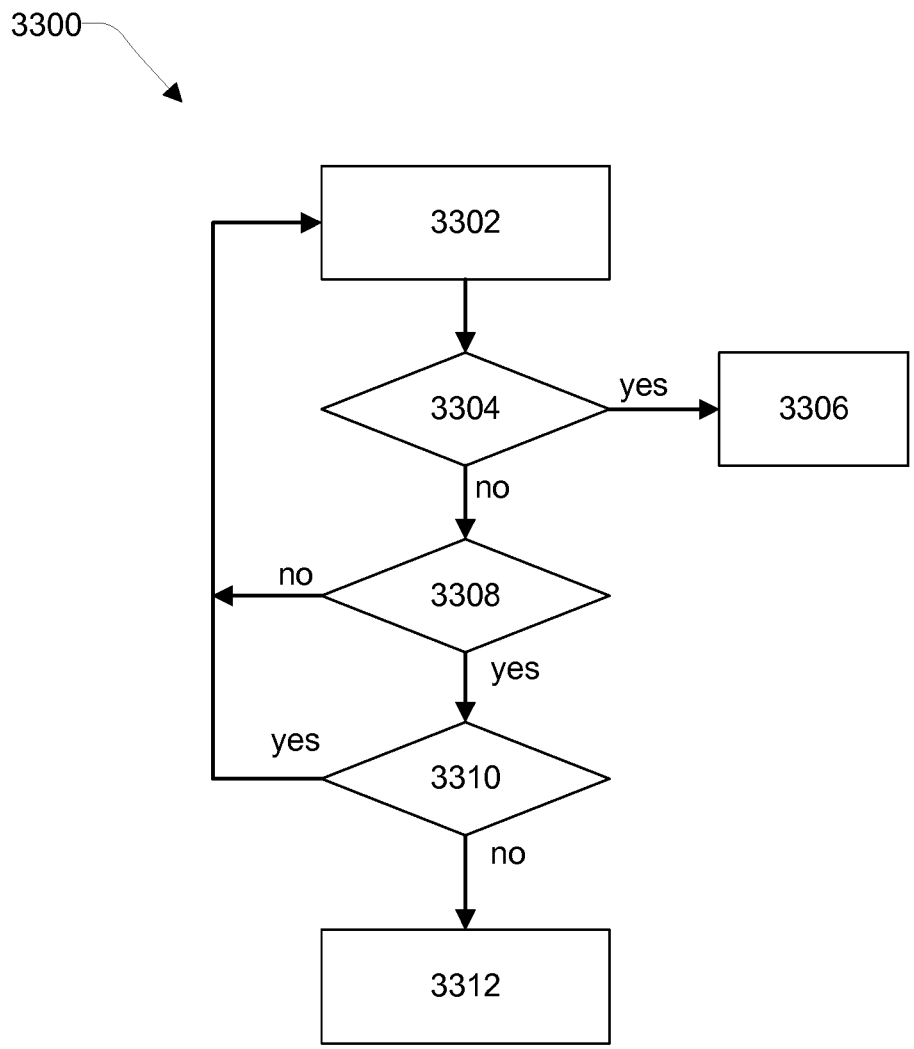
FIG. 11 shows a flow chart of an exemplary method.

FIG. 11 shows a flow chart of an exemplary method 3300 for moving the plunger rod of an auto injector.

Initially, the plunger rod is moved 3302, e.g. with a first plunger rod speed, e.g. in a first plunger rod direction.

The resistance against the movement of the plunger rod is monitored, such as continuously monitored. By a first resistance criterion 3304, it is determined whether resistance against movement of the plunger rod exceeds a second high resistance threshold. If the resistance against movement of the plunger rod does not exceed the second high resistance threshold (first resistance criterion 3304 is answered no), by a second resistance criterion 3308, it is determined whether resistance against movement of the plunger rod exceeds a first high resistance threshold. If the resistance against movement of the plunger rod does not exceed the first high resistance threshold (second resistance criterion 3304 is answered no), the movement of the plunger rod is continued 3302. The first plunger threshold may be lower than the second high resistance threshold.

The position of the plunger rod is monitored, such as continuously monitored. If the resistance against movement of the plunger rod does exceed the first high resistance threshold (second resistance criterion 3308 is answered yes), by a first position criterion 3310, it is determined whether the plunger rod has reached and/or passed a predetermined plunger rod position, such as a first plunger rod position, a second plunger rod position, a third plunger rod position, a fourth plunger rod position and/or a fifth plunger rod position (see e.g. FIGS. 7 and 9 for exemplary positions). If the plunger rod position has reached and/or passed the predetermined plunger rod position (first position criterion 3310 is answered yes), the movement of the plunger rod is continued 3302. Thus, the first high resistance threshold may be exceeded if the plunger rod has reached and/or passed the predetermined plunger rod position.

If the plunger rod position has not reached and/or passed the predetermined plunger rod position (first position criterion 3310 is answered no), the movement of the plunger rod is stopped 3312, and an error may be communicated to the user, e.g. via a user interface. Thus, an error may be assumed if the first high resistance threshold is exceeded before the plunger rod has reached and/or passed the predetermined plunger rod position.

Figure 12:
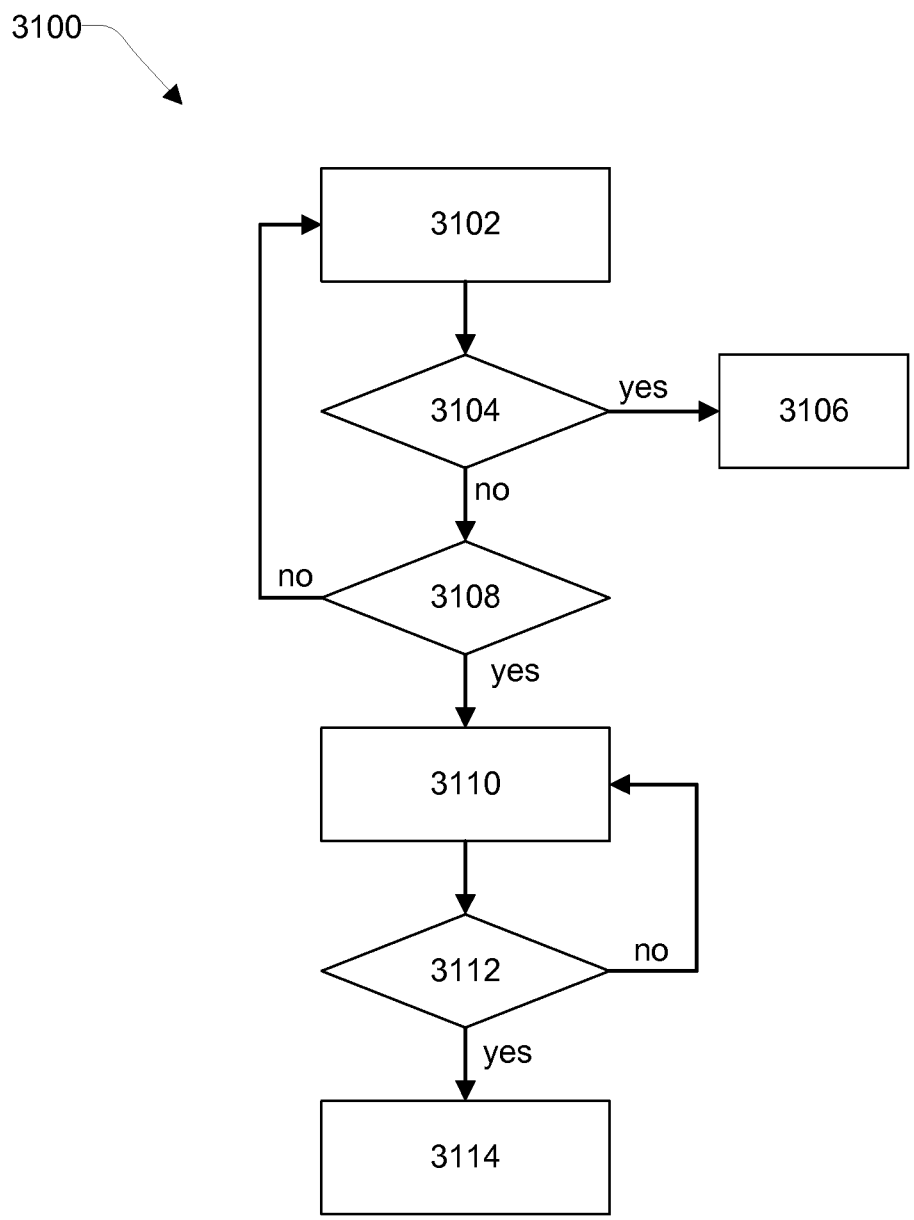
FIG. 12 shows a flow chart of an exemplary method.

If the resistance against movement of the plunger rod does exceed the second high resistance threshold (first resistance criterion 3304 is answered yes), the movement of the plunger rod is stopped 3306 and end of injection may be assumed. In stopping 3306 the movement of the plunger rod, the plunger rod may be locked in its position for a dwell time, e.g. to prevent a sudden drop in pressure in the cartridge, e.g. to prevent back flow of medicament FIG. 12 shows a flow chart of an exemplary method 3100 for moving the plunger rod of an auto injector.

Initially, the plunger rod is moved 3102 with a first plunger rod speed, e.g. in a first plunger rod direction.

The resistance against the movement of the plunger rod is monitored, such as continuously monitored. By a first resistance criterion 3104, it is determined whether resistance against movement of the plunger rod exceeds a first high resistance threshold. If the resistance against movement of the plunger rod does exceed the first high resistance threshold (first resistance criterion 3104 is answered yes), the movement of the plunger rod is stopped 3106 and an error may be communicated to the user, e.g. via a user interface.

The position of the plunger rod is monitored, such as continuously monitored. If the resistance against movement of the plunger rod does not exceed the first high resistance threshold (first resistance criterion 3104 is answered no), by a first position criterion 3108, it is determined whether the plunger rod has reached and/or passed a predetermined plunger rod position, such as a first plunger rod position, a second plunger rod position, a third plunger rod position, a fourth plunger rod position and/or a fifth plunger rod position (see e.g. FIGS. 7 and 9 for exemplary positions). If the plunger rod position has not reached and/or passed the predetermined plunger rod position (first position criterion 3108 is answered no), the movement of the plunger rod is continued 3102 with the first plunger rod speed.

If the plunger rod position has reached and/or passed the predetermined plunger rod position (first position criterion 3108 is answered yes), the plunger rod is moved 3110 with a second plunger rod speed, e.g. in the first plunger rod direction. The second plunger rod speed may be lower than the first plunger rod speed. By lowering the plunger rod speed, the amount of medicament needing to be forced though the needle per time, is reduced, thereby reducing the amount of force needed to advance the stopper.

By a second resistance criterion 3112, it is determined whether resistance against movement of the plunger rod exceeds a second high resistance threshold. If the resistance against movement of the plunger rod does not exceed the second high resistance threshold (second resistance criterion 3112 is answered no), the movement of the plunger rod is continued 3110 with the second plunger rod speed.

If the resistance against movement of the plunger rod does exceed the second high resistance threshold (second resistance criterion 3112 is answered yes), the movement of the plunger rod is stopped 3114 and end of injection may be assumed. In stopping 3114 the movement of the plunger rod, the plunger rod may be locked in its position for a dwell time, e.g. to prevent a sudden drop in pressure in the cartridge, e.g. to prevent back flow of medicament.

Figure 13:
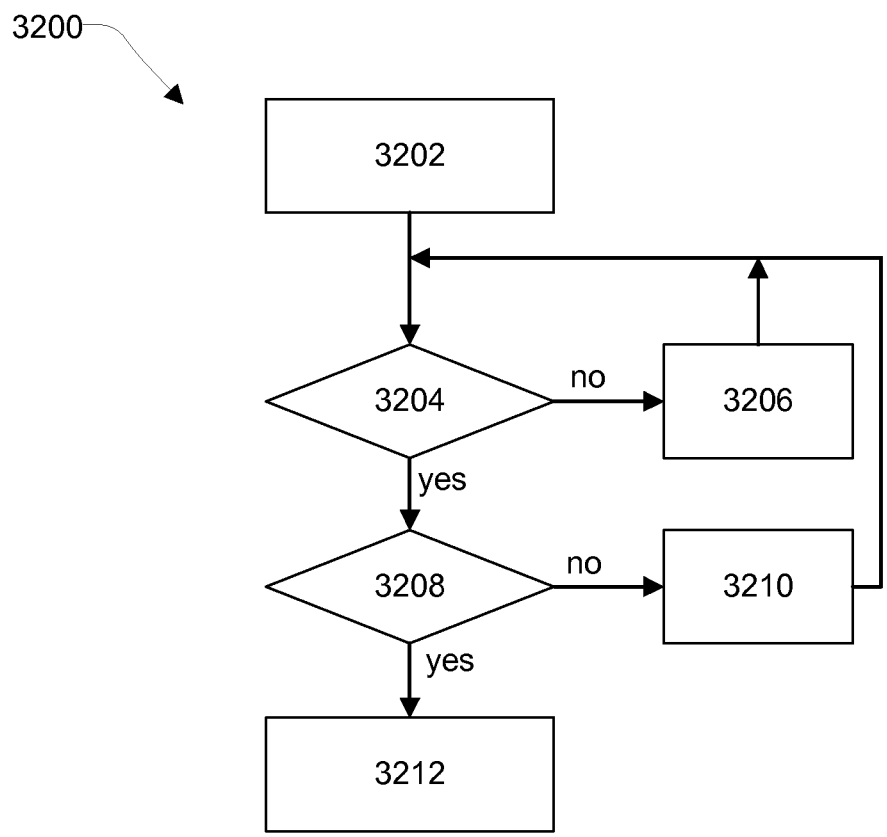
FIG. 13 shows a flow chart of an exemplary method.

FIG. 13 shows a flow chart of an exemplary method 3200 for moving the plunger rod of an auto injector.

Initially, the plunger rod is moved 3202, e.g. with a first plunger rod speed, e.g. in a first plunger rod direction.

The resistance against the movement of the plunger rod is monitored, such as continuously monitored. By a resistance criterion 3204, it is determined whether resistance against movement of the plunger rod exceeds a high resistance threshold, such as a first high resistance threshold and/or a second high resistance threshold.

If the resistance against movement of the plunger rod does not exceed the high resistance threshold (resistance criterion 3204 is answered no), the speed of the movement of the plunger rod is increased 3206.

If the resistance against movement of the plunger rod does exceed the high resistance threshold (resistance criterion 3204 is answered yes), it is determined by a speed criteria 3208 whether the plunger rod speed is zero, i.e. the plunger rod is not moving.

If the plunger rod speed is not zero (speed criteria 3208 is answered no) the plunger rod speed is reduced 3210. If the plunger rod speed is zero (speed criteria 3208 is answered yes) the process is stopped 3212. In stopping 3212, the plunger rod may be locked in its position for a dwell time, e.g. to prevent a sudden drop in pressure in the cartridge, e.g. to prevent back flow of medicament.

The high resistance threshold of resistance criterion 3204 may be determined based on the position of the plunger rod. The plunger rod position may also be used to determine whether in stopping 3212 the process, the medicament has been expelled sufficiently and/or an error caused the process to stop too early. A corresponding message may be provided to the user, e.g. via the user interface.

By the method 3200, the speed is adjusted to be as high as possible without exceeding the resistance thresholds.

Figure 14:
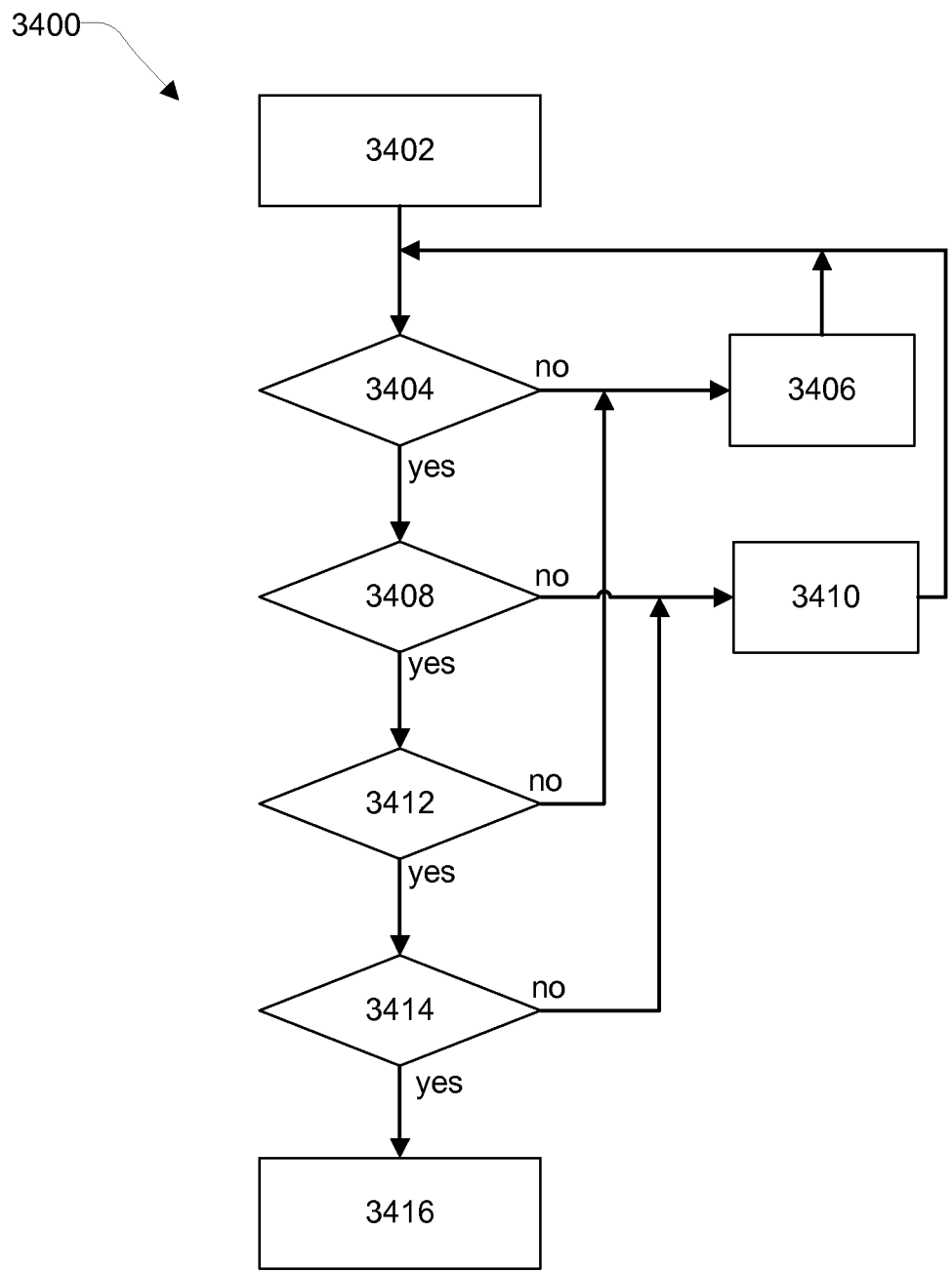
FIG. 14 shows a flow chart of an exemplary method.

FIG. 14 shows a flow chart of an exemplary method 3400 for moving the plunger rod of an auto injector.

Initially, the plunger rod is moved 3402, e.g. with a first plunger rod speed, e.g. in a first plunger rod direction.

The resistance against the movement of the plunger rod is monitored, such as continuously monitored. By a first resistance criterion 3404, it is determined whether resistance against movement of the plunger rod exceeds a first high resistance threshold.

If the resistance against movement of the plunger rod does not exceed the first high resistance threshold (first resistance criterion 3404 is answered no), the speed of the movement of the plunger rod is increased 3406.

The position of the plunger rod is monitored, such as continuously monitored. If the resistance against movement of the plunger rod does exceed the first high resistance threshold (first resistance criterion 3404 is answered yes), by a first position criterion 3408, it is determined whether the plunger rod has reached and/or passed a predetermined plunger rod position, such as a first plunger rod position, a second plunger rod position, a third plunger rod position, a fourth plunger rod position and/or a fifth plunger rod position (see e.g. FIGS. 7 and 9 for exemplary positions).

If the plunger rod position has not reached and/or passed the predetermined plunger rod position (first position criterion 3408 is answered no), the speed of the movement of the plunger rod is decreased 3410.

If the plunger rod position has reached and/or passed the predetermined plunger rod position (first position criterion 3408 is answered yes), the movement of the plunger rod may be continued. Thus, the first high resistance threshold may be exceeded if the plunger rod has reached and/or passed the predetermined plunger rod position. In this case, by a second resistance criterion 3412, it is determined whether resistance against movement of the plunger rod exceeds a second high resistance threshold.

If the resistance against movement of the plunger rod does not exceed the second high resistance threshold (second resistance criterion 3412 is answered no), the speed of the movement of the plunger rod is increased 3406.

If the resistance against movement of the plunger rod does exceed the second high resistance threshold (second resistance criterion 3412 is answered yes), it is determined by a speed criteria 3414 whether the plunger rod speed is zero, i.e. the plunger rod is not moving.

If the plunger rod speed is not zero (speed criteria 3414 is answered no) the plunger rod speed is reduced 3410. If the plunger rod speed is zero (speed criteria 3414 is answered yes) the process is stopped 3416. In stopping 3416, the plunger rod may be locked in its position for a dwell time, e.g. to prevent a sudden drop in pressure in the cartridge, e.g. to prevent back flow of medicament. In stopping 3416 end of injection may be assumed.

By the method 3400, the speed is adjusted to be as high as possible without exceeding the resistance thresholds.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 2 system
4 auto injector
6 housing
10 battery
20 processing unit
22 orientation sensor
24 code sensor
26 plunger rod position sensor
28 cartridge sensor
30 needle sensor
32 temperature sensor
34 resistance sensor
300 cartridge receiver
301 cartridge receiver opening
304 receiving direction
400 plunger rod
402 inner plunger rod
404 outer plunger rod
500 drive module
502 motor
600 cartridge assemply
700 cartridge
701 dual chamber cartridge
702 cartridge component
704 first cartridge subcomponent
706 second cartridge subcomponet
708 first stopper
710 second stopper
712 bypass section
714 cartridge outlet
716 cartridge back face
718 first end
720 second end
722 first stopper direction
800 cartridge holder
808 cartridge retention member
812 needle assembly coupling portion
900 needle assembly
902 needle
904 needle hub
906 cartridge holder coupling portion
908 needle cover
1000 cartridge code feature
1100 user interface
1102 concact member
1108 first input member
1110 first output member
1200 resistance graph
1200X position axis
1200Y resistance axis
1201 first high resistance threshold
1202 second high resistance threshold
1204 third high resistance threshold
1206 first slope
1208 second slope
1210 third slope
1220 first plunger rod position
1222 second plunger rod positon
1223 third plunger rod position
1224 fourth plunger rod position
1226 fifth plunger rod position
1228 retracted plunger rod position
1229 extended plunger rod position
1240 first plunger rod speed
1242 second plunger rod speed
1300 speed graph
1300X position axis
1300Y speed axis
3000 method
3001 receiving
3002 moving
3004 determining
3006 receiving
3010 adjusting
3100 method
3102 move plunger rod at first speed
3104 first resistance criteria
3106 stop movement of plunger rod
3108 first position criteria
3110 move plunger rod at second speed
3112 second resistance criteria
3114 stop movement of plunger rod
3200 method
3202 move plunger rod at first speed
3204 resistance criteria
3206 increase speed 3208 speed criteria
3210 decrease speed
3212 stop movement of plunger rod
3300 method
3302 move plunger rod at first speed
3304 first resistance criteria
3306 stop movement of plunger rod
3308 second resistance criteria
3310 first position criteria
3312 stop movement of plunger rod
3400 method
3402 move plunger rod at first speed
3404 first resistance criteria
3406 increase speed
3408 first position criteria
3410 decrease speed
3412 second resistance criteria
3414 speed criteria
3416 stop movement of plunger rod

The invention claimed is:

1. An auto-injector for administering a medicament, comprising:
   a housing;
   a cartridge receiver configured to receive a cartridge comprising a first stopper;
   a drive module coupled to move a plunger rod between a retracted plunger rod position and an extended plunger rod position, the plunger rod being configured to move the first stopper;
   a resistance sensor configured to provide a resistance signal indicative of resistance against movement of the plunger rod; and
   a processing unit coupled to the drive module and to the resistance sensor, the processing unit being configured to:
      control the drive module to move the plunger rod towards the extended plunger rod position with a plunger rod speed;
      determine plunger rod position;
      receive the resistance signal; and
      control the drive module so as to adjust movement of the plunger rod if the resistance signal is indicative of resistance against movement of the plunger rod above a high resistance threshold, wherein the high resistance threshold is determined by the plunger rod position,
      wherein the high resistance threshold is a first high resistance threshold when the plunger rod position is between the retracted plunger rod position and a first plunger rod position, wherein the plunger rod is in engagement with the first stopper at the first plunger rod position, and wherein the high resistance threshold is a second high resistance threshold when the plunger rod position is between a second plunger rod position and the extended plunger rod position, wherein the plunger rod is in engagement with the first stopper at the second plunger rod position, and wherein the second high resistance threshold is higher than the first high resistance threshold, wherein the first stopper is positioned at a retracted stopper position when the plunger rod is at the retracted plunger rod position and a first stopper position when the plunger rod is at the first plunger rod position.

2. The auto injector according to claim 1, wherein the first high resistance threshold is between 50-80 N.

3. The auto injector according to claim 2, wherein the first high resistance threshold is 55 N.

4. The auto injector according to claim 1, wherein the second high resistance threshold is between 70-100 N.

5. The auto injector according to claim 4, wherein the second high resistance threshold is 80 N.

6. The auto injector according to claim 1, wherein the distance between the extended plunger rod position and the first plunger rod position is between 1-3 mm.

7. The auto injector according to claim 1, wherein the distance between the retracted plunger rod position and the first plunger rod position is between 0-60 mm.

8. The auto injector according to claim 1, wherein the distance between the retracted plunger rod position and the first plunger rod position is between 50-60 mm.

9. The auto injector according to claim 1, comprising a code sensor configured to read a cartridge code feature, the processing unit being coupled to the code sensor, the processing unit being configured to receive from the code sensor a code signal indicative of the cartridge code feature, and wherein the processing unit is configured to determine the first plunger rod position and/or the second plunger rod position based on the code signal.

10. The auto injector according to claim 1, wherein the resistance sensor is configured to determine electrical current through the drive module.

11. The auto injector according to claim 1, wherein the resistance sensor is configured to measure pressure and/or force applied to a plunger rod front end of the plunger rod.

12. The auto injector according to claim 1, comprising a tachometer configured to provide a tachometer signal indicative of a count of revolutions of the drive module, the processing unit being coupled to the tachometer, and the processing unit being configured to receive the tachometer signal and determine the plunger rod position based on the tachometer signal.

13. The auto injector according to claim 1, wherein adjusting the movement of the plunger rod comprises stopping the movement of the plunger rod.

14. The auto injector according to 13, wherein adjusting the movement of the plunger rod further comprises preventing movement of the plunger rod towards the retracted plunger rod position for a dwell time.

15. The auto injector according to claim 1, wherein adjusting the movement of the plunger rod comprises moving the plunger rod to the retracted plunger rod position.

16. The auto injector according to claim 1, wherein adjusting the movement of the plunger rod comprises decreasing the plunger rod speed.

17. The auto injector according to claim 1, wherein the processing unit is further configured to control the drive module to readjust the movement of the plunger rod after adjusting the movement of the plunger rod, if the resistance signal is indicative of resistance against movement of the plunger rod below the high resistance threshold.

18. The auto injector according to claim 17, wherein readjusting the movement of the plunger rod comprises increasing the plunger rod speed.

19. The auto injector according to claim 1, wherein the plunger rod speed is based on the plunger rod position.

20. The auto injector according to claim 19, wherein the processing unit is configured to control the drive module to move the plunger rod through a third plunger rod position between the first plunger rod position and the second plunger rod position, and wherein the processing unit is configured to control the drive module to vary the plunger rod speed between a first value when the plunger rod position is between the retracted plunger rod position and a fourth plunger rod position, and a second value when the plunger rod position is between a fifth plunger rod position and the extended plunger rod position, and wherein the second value is lower than the first value.

21. The auto injector according to claim 19, wherein the processing unit is configured to control the drive module to move the plunger rod through a third plunger rod position between the first plunger rod position and the second plunger rod position, and wherein the processing unit is configured to control the drive module to vary the plunger rod speed between a first value when the plunger rod position is between the retracted plunger rod position and a fourth plunger rod position, and a second value when the plunger rod position is between a fifth plunger rod position and the extended plunger rod position, and wherein the second value is higher than the first value.

22. A system comprising an auto injector according to claim 1, and a cartridge comprising a first stopper, wherein the cartridge is configured to be received in the cartridge receiver.

23. The system according to claim 22, wherein the cartridge is a dual chamber cartridge.

24. An auto-injector for administering a medicament, comprising:
- a housing;
- a cartridge receiver configured to receive a cartridge comprising a first stopper;
- a drive module coupled to move a plunger rod between a retracted plunger rod position and an extended plunger rod position, the plunger rod being configured to move the first stopper;
- a resistance sensor configured to provide a resistance signal indicative of resistance against movement of the plunger rod; and
- a processing unit coupled to the drive module and to the resistance sensor, the processing unit being configured to:
  control the drive module to move the plunger rod towards the extended plunger rod position with a plunger rod speed;
  determine plunger rod position;
  receive the resistance signal; and
  control the drive module so as to adjust movement of the plunger rod if the resistance signal is indicative of resistance against movement of the plunger rod above a high resistance threshold, wherein the high resistance threshold is determined by the plunger rod position,
  wherein the high resistance threshold is a first high resistance threshold when the plunger rod position is between the retracted plunger rod position and a first plunger rod position, and the high resistance threshold is a second high resistance threshold when the plunger rod position is between a second plunger rod position and the extended plunger rod position, and wherein the second high resistance threshold is higher than the first high resistance threshold;
wherein the high resistance threshold is a third high resistance threshold when the plunger rod position is between the first plunger rod position and the second plunger rod position, the third high resistance threshold is higher than the first high resistance threshold, and the third high resistance threshold is lower than the second high resistance threshold.

25. The auto injector according to claim 24, wherein the third high resistance threshold is increasing as the plunger rod position is moved from the first plunger rod position to the second plunger rod position.

* * * * *

UNITED STATES PATENT AND TRADEMARK OFFICE
CERTIFICATE OF CORRECTION

PATENT NO. : 11,684,724 B2
APPLICATION NO. : 16/607342
DATED : June 27, 2023
INVENTOR(S) : Henrik Egesborg It is certified that error appears in the above-identified patent and that said Letters Patent is hereby corrected as shown below:

In the Specification

In Column 19, Line 29, delete "medicament" and insert --medicament.--.

In Column 22, Line 2, delete "assemply" and insert --assembly--.

In Column 22, Line 7, delete "subcomponet" and insert --subcomponent--.

In Column 22, Line 26, delete "concact" and insert --contact--.

In Column 22, Line 39, delete "positon" and insert --position--.

In the Claims

In Column 24, Claim 14, Line 40, delete "to" and insert --to claim--.

Signed and Sealed this
Thirty-first Day of October, 2023

Katherine Kelly Vidal
*Director of the United States Patent and Trademark Office*